(12) United States Patent
Shahar et al.

(10) Patent No.: US 11,092,701 B1
(45) Date of Patent: Aug. 17, 2021

(54) SYSTEMS AND METHODS FOR IMPROVED MEDICAL IMAGING

(71) Applicant: GE Precision Healthcare LLC, Wauwatosa, WI (US)

(72) Inventors: Arie Shahar, Moshav Magshimim (IL); Roi Harpaz, Holon (IL); Elhanan Blaut, Netanya (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/922,791

(22) Filed: Jul. 7, 2020

(51) Int. Cl.
  *G01T 1/24* (2006.01)
  *G01T 1/29* (2006.01)
  *A61B 6/00* (2006.01)

(52) U.S. Cl.
  CPC ............ *G01T 1/249* (2013.01); *G01T 1/2921* (2013.01); *A61B 6/4258* (2013.01)

(58) Field of Classification Search
  CPC ........ G01T 1/247; G01T 1/249; A61B 6/4258
  See application file for complete search history.

(56) References Cited

U.S. PATENT DOCUMENTS

| | | |
|---|---|---|
| 2,257,361 A | 9/1941 | Yourkey |
| 3,206,652 A | 9/1965 | Monroe |
| 3,774,050 A | 11/1973 | Littwin |
| 4,419,618 A | 12/1983 | Gretsch |
| 4,421,986 A | 12/1983 | Friauf |
| 4,594,583 A | 6/1986 | Seko |
| 4,604,611 A | 8/1986 | Seko |
| 4,837,607 A | 6/1989 | Kemmer |

(Continued)

FOREIGN PATENT DOCUMENTS

| | | |
|---|---|---|
| DE | 3321921 A1 | 12/1984 |
| JP | S57201086 A | 12/1982 |

(Continued)

OTHER PUBLICATIONS

PCT Search Report and Written Opinion issued in connection with corresponding Application No. PCT/IL2014/050848 dated Feb. 5, 2015.

(Continued)

*Primary Examiner* — David P Porta
*Assistant Examiner* — Fani Boosalis
(74) *Attorney, Agent, or Firm* — The Small Patent Law Group LLC; Dean D. Small

(57) ABSTRACT

A radiation detector assembly is provided that includes a semiconductor detector, plural pixelated anodes disposed on a surface of the semiconductor detector, and at least one processor. Each pixelated anode is configured to generate a mixed primary signal responsive to reception of a photon by at least one surrounding anode of the pixelated anode and to generate a mixed secondary signal responsive to reception of a photon by the pixelated anode. The at least one processor is operably coupled to the pixelated anodes, and is configured to: acquire the mixed primary signal from a first pixelated anode; acquire the mixed secondary signal from a second pixelated anode; and count an event in the second pixelated anode responsive to acquiring the mixed primary signal from the first pixelated anode and the mixed secondary signal from the second pixelated anode.

20 Claims, 14 Drawing Sheets

(56) References Cited

U.S. PATENT DOCUMENTS

| | | | |
|---|---|---|---|
| 4,852,135 A | 6/1989 | Anisovich | |
| 4,885,620 A | 12/1989 | Kemmer | |
| 4,926,228 A | 5/1990 | Ashley | |
| 5,148,809 A | 9/1992 | Biegeleisen-Knight | |
| 5,239,179 A | 8/1993 | Baker | |
| 5,245,191 A | 9/1993 | Barber | |
| 5,273,910 A | 12/1993 | Tran | |
| 5,326,996 A | 7/1994 | McNutt | |
| 5,365,069 A | 11/1994 | Eisen | |
| 5,376,796 A | 12/1994 | Chan | |
| 5,504,334 A | 4/1996 | Jansen | |
| 5,561,330 A | 10/1996 | Crook | |
| 5,562,095 A | 10/1996 | Downey | |
| 5,672,954 A | 9/1997 | Watanabe | |
| 5,754,690 A | 5/1998 | Jackson | |
| 5,771,308 A | 6/1998 | Florent | |
| 5,813,712 A | 9/1998 | Mozelt | |
| 5,825,033 A | 10/1998 | Barrett | |
| 5,847,398 A | 12/1998 | Shahar | |
| 5,905,624 A | 5/1999 | Andreica | |
| 6,002,741 A * | 12/1999 | Eisen | G01T 1/2928 378/62 |
| 6,034,373 A | 3/2000 | Shahar | |
| 6,140,650 A | 10/2000 | Berlad | |
| 6,169,287 B1 | 1/2001 | Warburton | |
| 6,239,438 B1 | 5/2001 | Schubert | |
| 6,388,244 B1 | 5/2002 | Gagnon | |
| 6,535,229 B1 | 3/2003 | Kraft | |
| 6,618,185 B2 | 9/2003 | Sandstrom | |
| 6,748,044 B2 | 6/2004 | Sabol | |
| 6,943,355 B2 | 9/2005 | Shwartz | |
| 7,026,623 B2 | 4/2006 | Oaknin | |
| 7,187,790 B2 | 3/2007 | Sabol | |
| 7,381,959 B2 | 6/2008 | Manjeshwar | |
| 7,490,085 B2 | 2/2009 | Walker | |
| 7,495,228 B1 | 2/2009 | Albagli | |
| 7,508,509 B2 | 3/2009 | Lehtikoski | |
| 7,668,288 B2 | 2/2010 | Conwell | |
| 7,671,331 B2 | 3/2010 | Hefetz | |
| 7,692,156 B1 | 4/2010 | Nagarkar | |
| 8,269,180 B2 | 9/2012 | De Geronimo | |
| 8,280,124 B2 | 10/2012 | Dichterman | |
| 8,405,038 B2 | 3/2013 | Bouhnik | |
| 8,492,725 B2 | 7/2013 | Zilberstein | |
| 8,837,793 B2 | 9/2014 | Rousso | |
| 9,002,084 B2 | 4/2015 | Shahar | |
| 9,482,764 B1 | 11/2016 | Shahar | |
| 9,632,186 B2 | 4/2017 | Shahar | |
| 10,324,202 B1 | 6/2019 | Shahar | |
| 10,481,285 B1 | 11/2019 | Shahar | |
| 2002/0191828 A1 | 12/2002 | Colbeth | |
| 2003/0054563 A1 | 3/2003 | Ljungstrom | |
| 2003/0099026 A1 | 5/2003 | Sandstrom | |
| 2003/0128324 A1 | 7/2003 | Woods | |
| 2003/0153830 A1 | 8/2003 | Weinberg | |
| 2004/0021082 A1 | 2/2004 | Wong | |
| 2004/0174949 A1 | 9/2004 | Yamashita | |
| 2004/0195512 A1 | 10/2004 | Crosetto | |
| 2005/0139777 A1 | 6/2005 | Rostaing | |
| 2005/0145797 A1 | 7/2005 | Oaknin | |
| 2005/0251010 A1 | 11/2005 | Mistretta | |
| 2006/0086913 A1 | 4/2006 | Spahn | |
| 2006/0108532 A1 | 5/2006 | Ohana | |
| 2006/0113482 A1 | 6/2006 | Pelizzari | |
| 2006/0249682 A1 | 11/2006 | Hogg | |
| 2006/0285751 A1 | 12/2006 | Wu | |
| 2007/0018108 A1 | 1/2007 | Kitamura | |
| 2007/0023669 A1 | 2/2007 | Hefetz | |
| 2007/0025522 A1 | 2/2007 | Fenster | |
| 2007/0173719 A1 | 7/2007 | Haider | |
| 2007/0235657 A1 | 10/2007 | He | |
| 2007/0290142 A1 | 12/2007 | Du | |
| 2008/0001090 A1 | 1/2008 | Ben-Haim | |
| 2008/0029704 A1 | 2/2008 | Hefetz | |
| 2008/0033291 A1 | 2/2008 | Rousso | |
| 2008/0039721 A1 | 2/2008 | Shai | |
| 2008/0042070 A1 | 2/2008 | Levin | |
| 2008/0092074 A1 | 4/2008 | Cohen | |
| 2008/0149842 A1 | 6/2008 | El-Hanany | |
| 2008/0230709 A1 | 9/2008 | Tkaczyk | |
| 2009/0070121 A1 | 3/2009 | Leonelli | |
| 2009/0080601 A1 | 3/2009 | Tkaczyk | |
| 2009/0110144 A1 | 4/2009 | Takahashi | |
| 2010/0261997 A1 | 10/2010 | Ren | |
| 2010/0308817 A1 | 12/2010 | Vija | |
| 2011/0026685 A1 | 2/2011 | Zilberstein | |
| 2011/0103544 A1 | 5/2011 | Hermony | |
| 2011/0147594 A1 | 6/2011 | Scoullar | |
| 2011/0155918 A1 | 6/2011 | Bouhnik | |
| 2011/0204245 A1 | 8/2011 | Robert | |
| 2011/0210235 A1 | 9/2011 | Dierickx | |
| 2011/0240865 A1 | 10/2011 | Frach | |
| 2012/0108948 A1 | 5/2012 | Jansen | |
| 2012/0205542 A1 | 8/2012 | Goedicke | |
| 2013/0168567 A1 | 7/2013 | Wartski | |
| 2014/0048714 A1 | 2/2014 | Shahar | |
| 2014/0126793 A1 | 5/2014 | Ahn | |
| 2014/0158890 A1 | 6/2014 | Pistorius | |
| 2014/0163368 A1 | 6/2014 | Rousso | |
| 2014/0343400 A1 | 11/2014 | Takayama et al. | |
| 2015/0063671 A1 | 3/2015 | Shahar | |
| 2015/0131776 A1 | 5/2015 | Cho | |
| 2015/0192681 A1 | 7/2015 | Cho | |
| 2016/0245934 A1 | 8/2016 | Shahar | |
| 2017/0000448 A1 | 1/2017 | Hefetz | |
| 2017/0014096 A1 | 1/2017 | Bouhnik | |
| 2017/0269240 A1 | 9/2017 | Shahar | |
| 2017/0350995 A1 | 12/2017 | Stanchina | |

FOREIGN PATENT DOCUMENTS

| | | |
|---|---|---|
| JP | S60218870 A | 11/1985 |
| WO | 1997014060 A1 | 4/1997 |
| WO | 2008135994 A2 | 11/2008 |
| WO | 2009036078 A2 | 3/2009 |
| WO | 2014173812 A1 | 10/2014 |

OTHER PUBLICATIONS

Meikle et al., "Accelerated EM reconstruction in total-body PET: potential for improving tumour detectability," 1994, Physics in Medicine and Biology, vol. 39, pp. 1689-1704.

Park et al., "Performance of a high-sensitivity dedicated cardiac SPECT scanner for striatal uptake quantification in the brain based on analysis of projection data," Med. Phys. 40 (4), Apr. 2013.

Riddell et al., "Noise reduction in oncology FDG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-121.

International Search Report and Written Opinion dated Jul. 15, 2016 for corresponding PCT Application No. PCT/US2016/029465 filed Apr. 27, 2016 (11 pages).

Warburton, An Approach to Sub-Pixel Spatial Resolution in Room Temperature X-Ray Detector Arrays with Good Energy Resolution. X-ray Instrumentation Associates (XIA), 2513 Charleston Road STE 207, Mountain View, CA 94043-1607, USA.

Iwanczyk et al., "Photon Counting Energy Dispersive Detector Arrays for X-ray Imaging" IEEE Trans Nucl Sci. 2009 ; 56(3): 535-542. doi:10.1109/TNS.2009.2013709. (27 pages).

Zhu, "Digital Signal Processing Methods for Pixelated 3-D Position Sensitive Room-Temperature Semiconductor Detectors" (2012) p. 1-184, available at: https://deepblue.lib.umich.edu/handle/2027.42/91490.

Barrett, "Charge Transport in Arrays of Semiconductor Gamma-Ray Detectors,"H.H. Barrett, Physical Review Letters, vol. 75, No. 1, Jul. 1995.

Eskin, "Signals Induced in Semiconductor Gamma-Ray Imaging Detectors," J.D. Eskin, Journal of Applied Physics, vol. 85, No. 2, Jan. 1999.

(56) References Cited

OTHER PUBLICATIONS

Niemela, "High-Resolution p-i-n CdTe and CdZnTe X-Ray Detectors with Cooling and Rise-Time Discrimination," IEEE Transactions on Nuclear Science, vol. 43, No. 3, Jun. 1996.

* cited by examiner

SYSTEMS AND METHODS FOR IMPROVED MEDICAL IMAGING

RELATED APPLICATIONS

Background of the Invention

The subject matter disclosed herein generally relates to the field of radiation detectors, for example to semiconductor radiation detectors that may be used in medical imaging, such as, Nuclear Medicine (NM), Nuclear Imaging (NI) and Molecular Imaging (MI) and may be used in imaging systems, such as, nuclear and molecular imaging cameras, Single Photon Emission Computed Tomography (SPECT), Computed Tomography (CT) and Positron Emission Tomography (PET).

During fabrication of a detector, relatively large wafers may be processed. In the case of semiconductors, such as, for example, CdZnTe (CZT), only part of the area of the wafer may be suitable to be used as a detector. The wafers may be tested, with the portions suitable to be used as detectors cut out from the large wafers and tiled (or butted) together to produce relatively large detector modules. The portions of the wafers may be cut using a dicing process that leaves the sidewall pixels damaged and having relatively poorer performance than inland pixels. Previously, to improve the performance of the sidewall pixels, the sidewalls of the pixels were polished to remove the damage created by the dicing process, and/or insulative tape with a conductive strip was applied on the sidewalls. (See, e.g., U.S. Pat. Nos. 6,034,373 and 5,905,264.)

The methods disclosed in U.S. Pat. Nos. 6,034,373 and 5,905,264, and/or other methods including polishing of sidewalls may be effective in improving the performances of the sidewall pixels. However, such techniques may consume time and resources that increase the manufacturing cost and cycle-time of the detector's production.

In addition, the polishing process introduces the challenge of simultaneously maintaining good surface quality of the sidewalls and accurate dimensions of the parts that are diced out. Errors in the dimensions of the parts that are diced out may alter the pitch size between the pixels of the different parts that are butted together to produce the detector and cause imperfect registration between the detector pixels and its collimator.

BRIEF DESCRIPTION OF THE INVENTION

In one embodiment, a radiation detector assembly is provided that includes a semiconductor detector, plural pixelated anodes, and at least one processor. The semiconductor detector has sidewalls and a surface. The plural pixelated anodes are disposed on the surface of the semiconductor detector. Each pixelated anode is configured to generate a mixed primary signal responsive to reception of a photon by at least one surrounding anode of the pixelated anode and to generate a mixed secondary signal responsive to reception of a photon by the pixelated anode. The at least one processor is operably coupled to the pixelated anodes, and is configured to: acquire the mixed primary signal from a first pixelated anode; acquire the mixed secondary signal from a second pixelated anode, wherein the mixed primary signal and the mixed secondary signal are generated responsive to an event generated in the second pixelated anode and collected by the first pixelated anode; and count an event in the second pixelated anode responsive to acquiring the mixed primary signal from the first pixelated anode and the mixed secondary signal from the second pixelated anode.

In another embodiment, a method of imaging using a semiconductor detector is provided. The semiconductor detector has sidewalls and a surface with plural pixelated anodes disposed thereon. The method includes generating a mixed primary signal responsive to reception of a photon by at least one surrounding anode of a pixelated anode. The method also includes generating a mixed secondary signal responsive to reception of the photon by the pixelated anode. The method further includes acquiring the mixed primary signal from a first pixelated anode and acquiring the mixed secondary signal from a second pixelated anode. The mixed primary signal and the mixed secondary signal are generated responsive to an event generated in the second pixelated anode and collected by the first pixelated anode. Also, the method includes counting an event in the second pixelated anode responsive to acquiring the mixed primary signal from the first pixelated anode and the mixed secondary signal from the second pixelated anode.

In another embodiment, method is provided for providing a radiation detector assembly. The method includes forming semiconductor detector portions. The method also includes joining the semiconductor detector portions to form a semiconductor detector having sidewalls and a surface. The semiconductor detector has plural pixelated anodes disposed on the surface, with each pixelated anode configured to generate a mixed primary signal responsive to reception of a photon by at least one surrounding anode of the pixelated anode and to generate a mixed secondary signal responsive to reception of a photon by the pixelated anode. Also the method includes coupling the semiconductor detector to at least one processor. The at least one processor is configured to acquire a mixed primary signal from a first pixelated anode; acquire at least one mixed secondary signal from a second pixelated anode, wherein the mixed primary signal and the mixed secondary signal are generated responsive to an event generated in the second pixelated anode and collected by the first pixelated anode; and count an event in the second pixel responsive to acquiring the mixed primary signal from the first pixelated anode and the mixed secondary signal from the second pixelated anode.

DETAILED DESCRIPTION OF THE INVENTION

Figure 1:
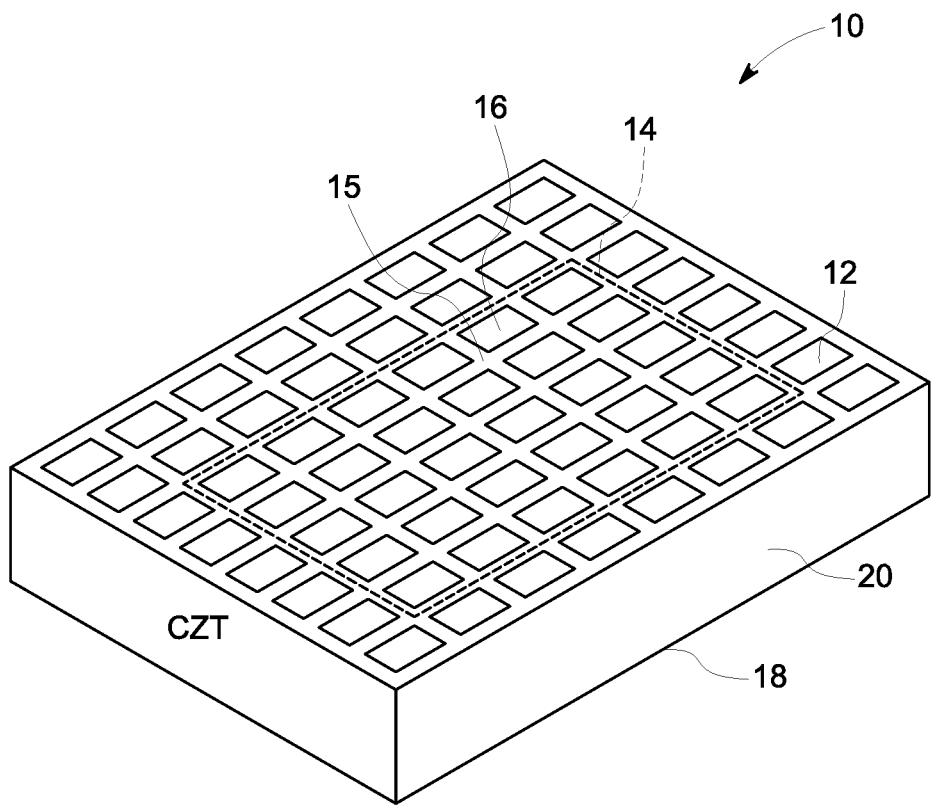
FIG. 1 provides a schematic illustration of a large dimension semiconductor wafer.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide radiation detectors with improved performances of sidewall pixels, for example, by electronic corrections. In various embodiments, electronic corrections are used to improve performance of bad inland pixels and/or to increase yield and reduce costs. Various embodiments provide for improved sidewall pixel performance without polishing of sidewalls. Accordingly, accurate dimension of detector portions may be maintained, enabling improved registration between detector pixels and corresponding collimators.

A technical effect provided by various embodiments includes improved performance of sidewall pixels and/or bad inland pixels. A technical effect of various embodiments includes reduced time and cost for assembling radiation detector assemblies.

Before addressing specific examples of the present disclosure, conventional primary and secondary (non-collected induced) signals are discussed. In various embodiments, as discussed below, electronic corrections are based on mixed primary and mixed secondary (non-collected induced) signals. Conventional primary and secondary signals, as the terms are used herein, differ from mixed primary and secondary signals. A conventional primary signal is the signal produced on an anode of a pixel under which a corresponding event is produced. In a case of a conventional primary signal, the electrical charge of the event is collected by the same anode under which event was produced. A conventional secondary (non-collected induced) signal is the signal produced by the primary event on the anode(s) of a pixel that is adjacent to the pixel in which the event is produced and collected. The conventional non-collected induced signals may also be referred to as conventional secondary signals.

FIG. 1 is a schematic illustration of a large dimension semiconductor wafer 10. The depicted wafer 10 is made of a CZT semiconductor plate 20. The depicted large wafer 10 is shown after fabrication has been completed, with the wafer including pixilated anode contacts 12 and a monolithic cathode contact 18 that have been applied on the CdZnTe (CZT) semiconductor bulk (plate) 20.

A preliminary detector made of wafer 10 may be electrically tested under radiation, with each pixel defined by the anodes 12 characterized to verify that its performance meet certain specified performance parameters. In various embodiments, during this test, good pixels 12 (e.g., those that meet the specified performance parameters) are mapped. In the illustrated embodiments, this mapping shows portion 15 confined inside frame 14, shown by a broken line, which is a region that includes pixels 16 that are pixels 12 for which most (e.g., meeting or exceeding a predetermined threshold percentage) meet the specified performance parameters. Portion 15 may then be used as a part or portion that is tiled together with portions 15 from other wafers that have been tested to fabricate an entire whole radiation detector module.

Figure 2A:
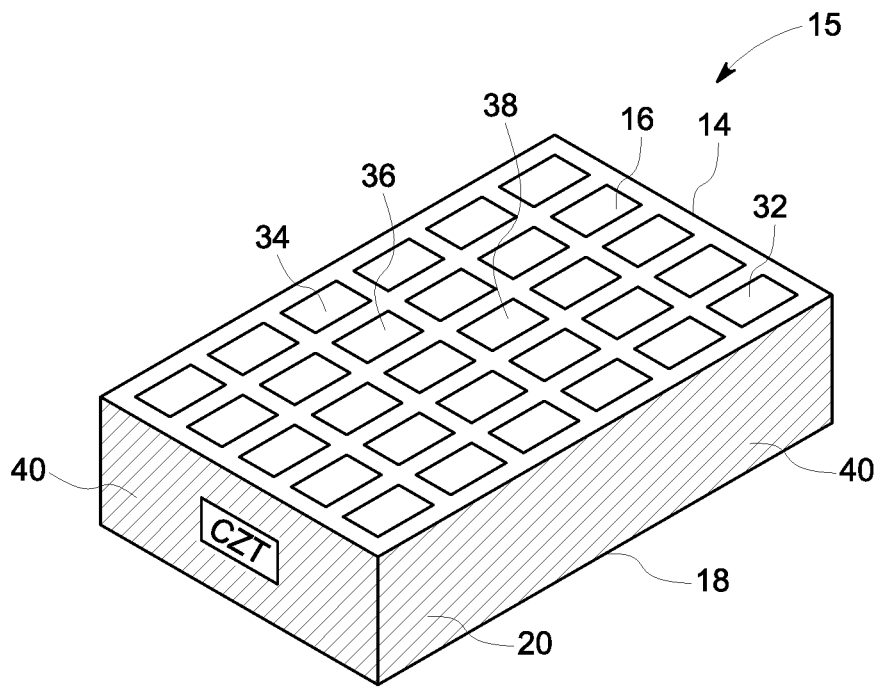
FIG. 2A provides a schematic illustration of a region removed from the wafer of FIG. 1.

FIG. 2A schematically shows the portion 15 after it was diced out of the larger wafer 10 of FIG. 1 along the lines of frame 14. The same reference numerals are used in FIGS. 1 and 2 to indicate corresponding components and features. The portion 15 includes sidewalls 40 of bulk 20 that are oriented along the lines of frame 14, along with pixels 16 on a top surface of the portion 15. The bottom surface of the portion 15 contains the monolithic cathode 18. In the illustrated embodiments, different types of pixels 16 are shown: corner pixels 32, first order sidewall pixels 34, which are aligned along sidewalls 40 and immediately adjacent to sidewalls; second order sidewall pixels 36, which are one pixel away from sidewalls 40; and inland pixels 38. As discussed below, first order sidewall pixels 34 are affected the most by sidewalls 40. The second order sidewall pixels 36 are still affected by sidewalls 40 but to a lesser extent than first order sidewall pixels 34. In various embodiments, the diced sidewalls 40 have a strong effect on the performance of the first order sidewall pixels 34 and a minor influence on the performance of second order sidewall pixels 36.

It may be noted that sidewalls 40 tend to be damaged by the dicing process and have a relatively high density of surface and sub-surface defects. These defects reduce the electrical resistivity of sidewalls 40. As explained below, this resistivity reduction causes the sidewall pixels to be biased by lower voltage relative to other pixels 16. In addition, sidewalls 40 break the symmetry of the first and the second order sidewall pixels 34 and 36 in various ways. For example, the first and second order pixels have adjacent pixels inside portion 15 but do not have adjacent pixels outside portion 15. Also, the dielectric constant inside portion 15 is much higher than the dielectric constant of air.

Figure 2B:
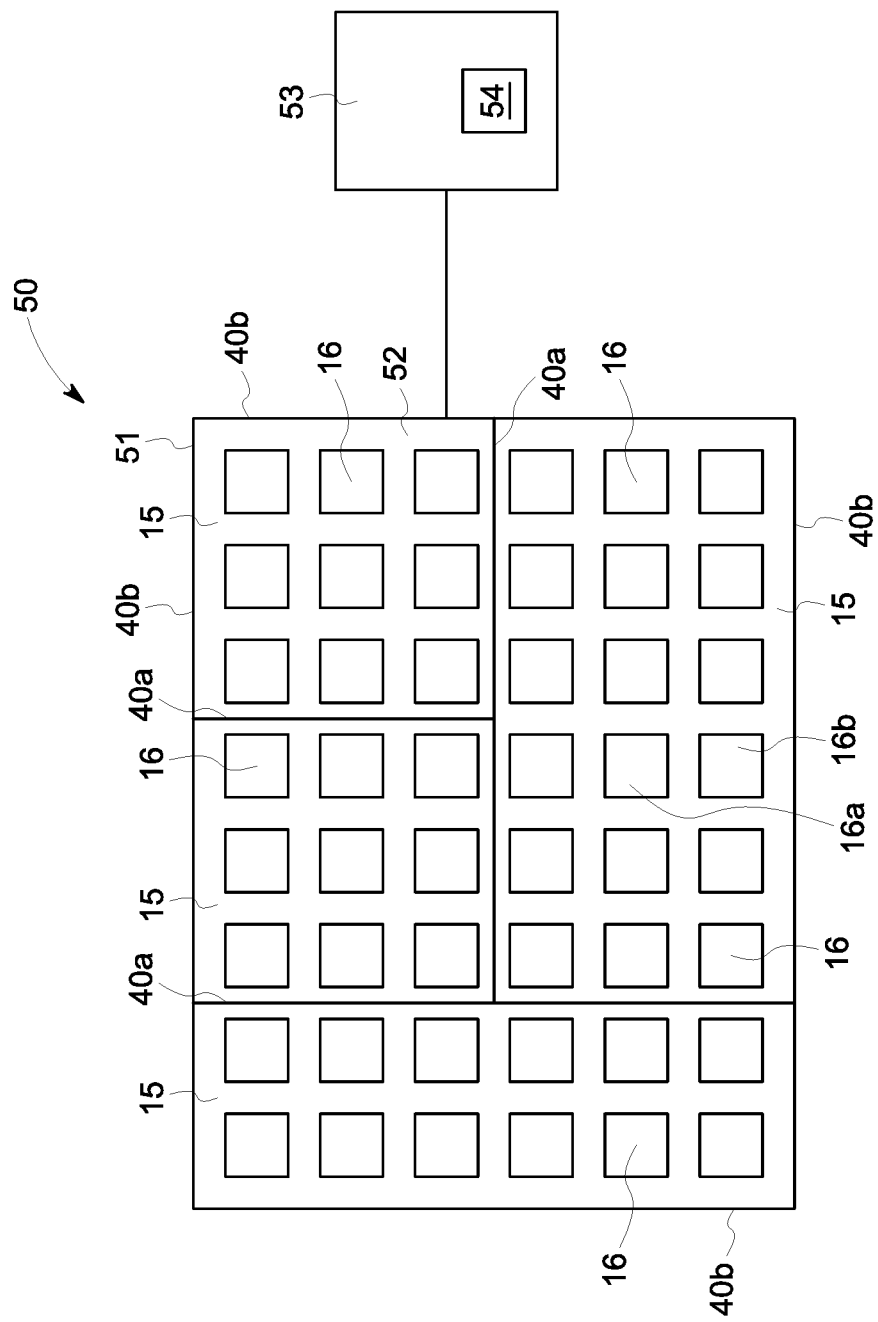
FIG. 2B provides a schematic block diagram of a system in accordance with various embodiments.

FIG. 2B provides a schematic block diagram of a radiation detector assembly 50 formed using a number of portions 15. As seen in FIG. 2B, the depicted example radiation detector assembly 50 includes a semiconductor detector 51, plural pixelated anodes 16 (see also FIGS. 1 and 2A), and a processing unit 53.

The semiconductor detector 51 has sidewalls 40 and a surface 52. The semiconductor detector 51 is made up of a number of portions 15 that have been diced from larger wafers and butted or tiled together to form the semiconductor 51. Because the sides of each portion 15 are defined by sidewalls 40, and some portions 15 are butted together in an interior portion of the semiconductor detector 51, the semiconductor detector 51 has interior sidewalls 40a that are disposed facing corresponding sidewalls 40a of adjacent portions 15, and also has exterior sidewalls 40b that face an exterior of the semiconductor detector 51. When the semiconductor detector 51 is assembled from the various portions, the pixelated anodes 16 that are next to sidewalls 40 (either interior or exterior) may be mapped (e.g., identified and having their location stored for later reference). Further, any inland pixelated anodes that are bad (e.g., do not meet a prescribed performance standard) may be mapped additionally or alternatively.

The plural pixelated anodes 16 are disposed on the surface 52. Generally, the pixelated anodes 16 generate electrical signals responsive to reception of photons by the radiation detector assembly 50. In the depicted embodiment, each pixelated anode 16 is configured to generate a mixed primary signal responsive to reception of a photon by at least one surrounding anode of the pixelated anode 16, and to generate a mixed secondary signal responsive to reception of a photon by the pixelated anode 16 itself.

In the illustrated embodiment, a mixed primary signal generated by a first pixel 16a starts as a conventional secondary signal induced by an electrical charge of an event (e.g., a photon absorbed under the anode of second pixel 16b) generated in a second pixelated anode 16b, and ends as a conventional primary signal in the first pixelated anode 16a. Also, a mixed secondary signal generated by the second pixel 16b starts as a conventional primary signal responsive to an event in the second pixelated anode 16b and ends as a conventional secondary signal induced on second anode 16b by an electrical charge of the event that ends under the first pixelated anode 16a. In the illustrated example, the second pixelated anode 16b is closer to a sidewall than the first pixelated anode 16a. More details regarding the formation or generation of mixed primary signals and mixed secondary signals are discussed in subsequent portions of this disclosure.

The processing unit 53 is configured (e.g., programmed) to acquire mixed primary signals and mixed secondary signals from the pixels 16, and to count events for the radiation detector assembly 50 using the mixed primary signals and mixed secondary signals. In the illustrated example, the processing unit 53 acquires (e.g., receives) the mixed primary signal from the first pixelated anode 16a, and acquires the mixed secondary signal from the second pixelated anode 16b. (The mixed primary signal from the first pixelated anode 16a and the mixed secondary signal from the second pixelated anode 16b are for an event generated in the second pixelated anode 16b and collected by the first pixelated anode 16a.) The processing unit 53 then counts the event for the second pixel 16b, responsive to acquiring the mixed primary signal from the first pixelated anode 16a and the mixed secondary signal from the second pixelated anode 16b. For example, the event may be counted for the second pixel 16b responsive to acquiring a mixed primary signal for the first pixelated anode and a mixed secondary signal for the second pixelated anode simultaneously. A number of events counted over a period of time may be used to reconstruct an image.

Generally, in various embodiments the processing unit 53 includes processing circuitry configured to perform one or more tasks, functions, or steps discussed herein. It may be noted that "processing unit" as used herein is not intended to necessarily be limited to a single processor or computer. For example, the processing unit 53 may include multiple processors, ASIC's, FPGA's, and/or computers, which may be integrated in a common housing or unit, or which may distributed among various units or housings. It may be noted that operations performed by the processing unit 53 (e.g., operations corresponding to process flows or methods discussed herein, or aspects thereof) may be sufficiently complex that the operations may not be performed by a human being within a reasonable time period. For example, the determination of values of charges may rely on or utilize computations that may not be completed by a person within a reasonable time period.

The depicted processing unit 53 includes a memory 54. The memory 54 may include one or more computer readable storage media. The memory 54, for example, may store mapping information describing the locations of sidewalls and/or bad pixels, acquired emission information, image data corresponding to images generated, results of intermediate processing steps, calibration parameters or calibration information, or the like. Further, the process flows and/or flowcharts discussed herein (or aspects thereof) may represent one or more sets of instructions that are stored in the memory 54 for direction of operations of the radiation detection assembly 50.

Figure 3:
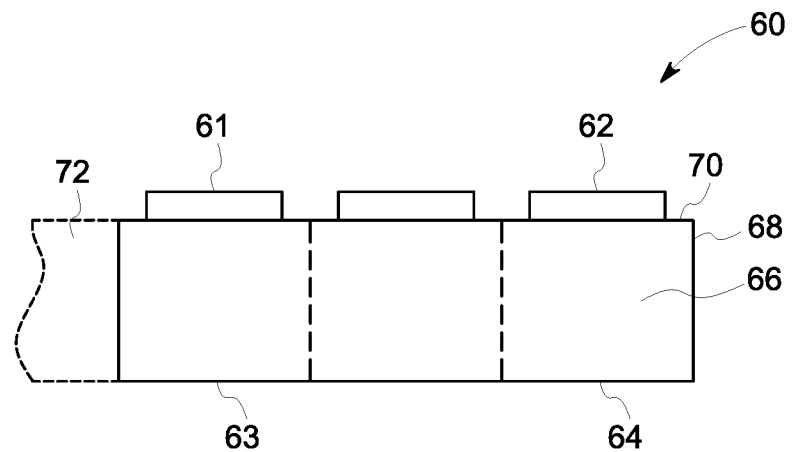
FIG. 3 provides a schematic side view of a radiation detector in accordance with various embodiments.
Figure 4:
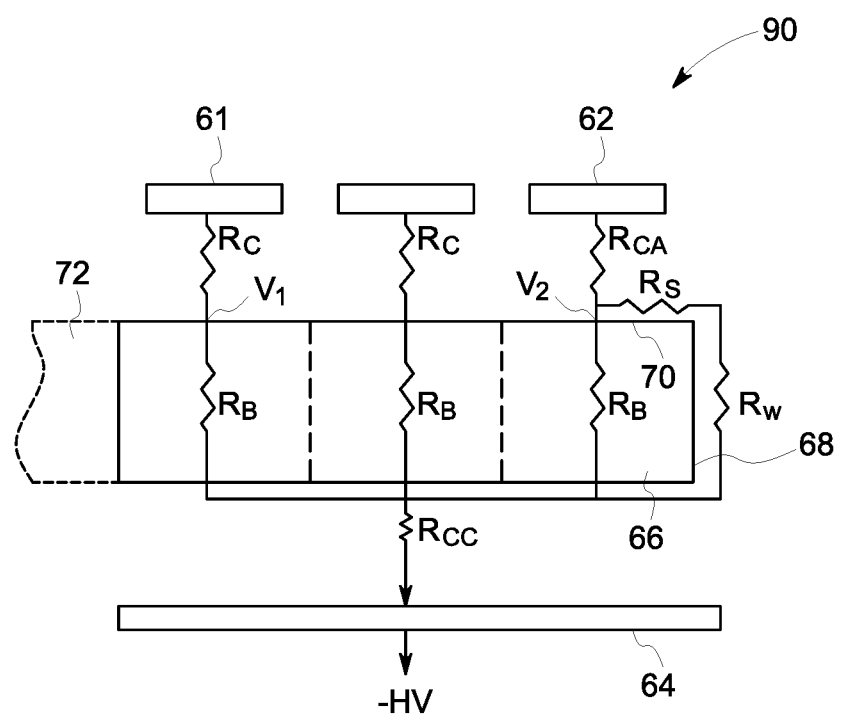
FIG. 4 provides a schematic view of an equivalent electrical circuit of the radiation detector of FIG. 3.

FIGS. 3 and 4 help explain effects created by sidewalls 40 mentioned above on sidewall pixels 34 and 36. FIGS. 3 and 4 provide a schematic side view illustration of a radiation detector 60 and its equivalent electrical circuit 90, respectively. The same reference numerals are used to indicate the same components and features in FIGS. 3 and 4.

The depicted example radiation detector 60 of FIG. 3 includes pixelated anodes 62 on a top surface of semiconductor bulk 66 and pixels/voxels 63 under these anodes 62. A monolithic cathode 64 is applied on the bottom surface of semiconductor bulk 66. Diced sidewalls 68 are at a distance 70 from first order sidewall pixel 62. While inland pixel 61 may appear close to the edge of detector 60, this is not the case, as inland pixel 61 is not a sidewall pixel, with portion 72 shown by a broken line representing many pixels between inland pixel 61 and sidewalls 68 of detector 60.

FIG. 4 schematically shows radiation detector 60 with its components schematically separated. This depicted separation is shown for illustrative purposes only for the clarification of the electrical equivalent circuit 90 of detector 60, and does not represent the actual assembly of the components of radiation detector 60.

As seen in FIG. 4, Resistor $R_{CA}$ represents the contact resistance between pixelated anode 62 and semiconductor bulk 66. Resistor $R_B$ represents the resistance of semiconductor bulk 66 between pixelated anode 62 and monolithic cathode 64. Resistor $R_s$ represents the surface resistance between pixelated anode 62 and sidewall 68. Resistor $R_W$ represents the surface resistance of semiconductor bulk 66 along wall 68 between the upper and the lower surfaces of bulk 66. Also, Resistor $R_{CC}$ represents the contact resistance between monolithic cathode 64 and bulk 66.

According to the voltage divider for first order sidewall pixel 62, the voltage $V_2$ on bulk 66 under pixilated anode 62 is equal to:

$$V_2 = V \cdot \frac{R_T}{(R_T + R_{CA} + R_{CC})} \quad \text{Eq (1)}$$

where V is the high voltage (−HV) applied between anodes, such as anodes 61 and 62, and cathode 64, $R_T$ is the total resistance of $R_B$ connected in parallel to $R_S$ and $R_W$, which are connected in series. $R_T$ is given by:

$$R_T = \frac{R_B \cdot (R_S + R_W)}{(R_B + R_S + R_W)} \quad \text{Eq (2)}$$

According to Eq. (2), $R_B$ always satisfies:

$$R_B > R_T \quad \text{Eq(3)}$$

According to the voltage divider for inland pixel 61, the voltage $V_1$ on bulk 66 under pixilated anode 61 is equal to:

$$V_1 = V \cdot \frac{R_B}{(R_B + R_{CA} + R_{CC})} \quad \text{Eq (4)}$$

If the walls 68 are diced and the top surface of bulk 66 is polished, both will include a relatively high density of defects and thus, the surface resistances $R_S$ and $R_W$ are both much smaller than $R_B$ thus:

$$R_B \gg R_T \quad \text{Eq(5)}$$

In such a case:

$$V_2 < V_1 \quad \text{Eq(6)}$$

With $V_2$ much lower than $V_1$, the pixelated anode 61 associated with $V_1$ will attract events moving under anode 62 and from near the sidewall (e.g., events originating in pixelated anode 62 associated with $V_2$.

Figure 5:
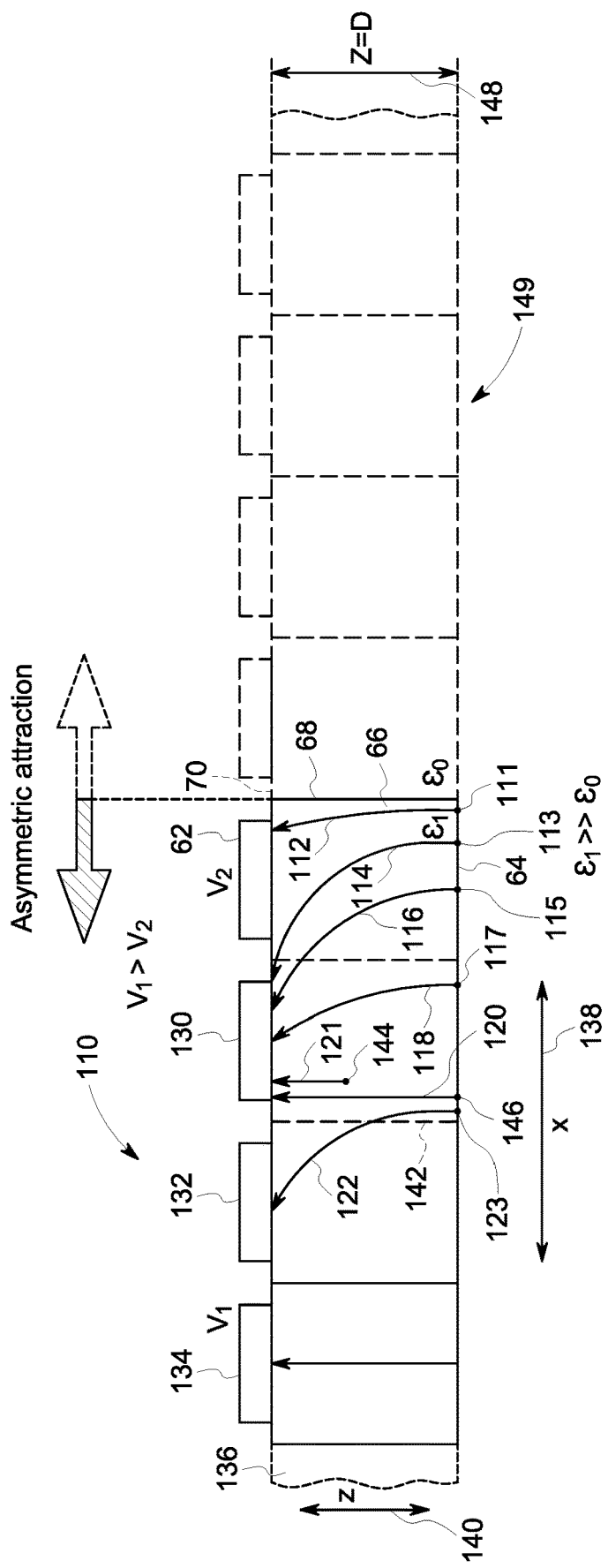
FIG. 5 provides a schematic illustration of a radiation detector including a pixel 134 that is far away from the edge of the radiation detector and its sidewalls.

FIG. 5 is a schematic illustration of a radiation detector 110 having a broken portion 136 indicating that a pixel 134 is far away from the edge of the radiation detector 110 and its sidewalls 68. The same components in FIGS. 3, 4 and 5 are indicated by the similar reference numerals.

The radiation detector 110 includes first order sidewall pixels 62 that, as explained above and shown in Eq. (6), are biased by voltage $V_2$ that is lower than the bias voltage $V_1$ of inland pixels 134. The lower voltage of bias voltage $V_2$ on pixels 62 causes an attraction that acts on the electrical charges of events 111, 113 and 115 under pixel 62, attracting the corresponding charges toward adjacent inner pixels 130, 132 and 134.

The dielectric constant of bulk 66 $\varepsilon_1$ is much larger than the dielectric constant $\varepsilon_0$ of the air ($\varepsilon_1 \gg \varepsilon_0$). When $\varepsilon_1 \gg \varepsilon_0$, the air region acts as a confinement region for the electrical field of the detector and repels the electrical fields lines away from walls 68 and into the bulk 66 and toward pixels 130, 132 and 134.

Also, part 149 of detector 110, shown by broken lines, represents the part of wafer 10 that has been removed by the dicing of walls 68 to create a part of a detector module such as portion 15 of FIG. 2. Dicing the walls 68 in wafer 10 of FIG. 1 removes part 149 of wafer 10 of FIG. 1 that otherwise would be adjacent to pixels 62 that would be, in such a situation, inland pixels with adjacent pixels on both sides. Accordingly, walls 68 cause sidewall pixels 68 to be in an asymmetric arrangement when pixels 62 have adjacent pixels, such as pixels 130, 132 and 134, on one side, and no adjacent pixels on the other side (the air side). Similarly, second order sidewall pixels, such as pixels 36 of FIG. 2, have more adjacent pixels on one side than the other side. The asymmetric arrangement where pixels 62 have more adjacent pixels on one side causes an attraction force that acts on the electrical charges of the events, such as events 111, 113 and 115 under pixels 62, toward adjacent inner pixels 130, 132 and 134.

The above mentioned phenomena (i.e., $V_2 < V_1$, $\varepsilon_1 \gg \varepsilon_0$ and the asymmetric arrangement in which the sidewalls pixels 62 or 36 have more adjacent pixels on one side) cause the lines of the electrical field in the detector bulk 66 to bend inward from sidewall pixels 62 into inner adjacent pixels 130, 132 and 134.

The lines of the electrical field in the detector bulk 66 are the trajectories along which the electrons move in the charge clouds of the events generated, by radiation absorption under pixel 62. The electrical field in bulk 66 of detector 110 is produced by the high voltage (−HV) bias creating the electrical potential between positive anodes 62, 130, 132 and 134 and negative cathode 64.

Accordingly, for example, the electrons in the charge clouds of the events, such as event 111 under first order sidewall pixel 62 generated near sidewalls 68, move along field line 112 and are collected by anode 62. The electrons in the charge clouds of the events, such as event 113 generated under the center of first order side wall pixel 62, move along field line 114 and are collected by anode 130 that is adjacent to anode 62. The electrons in the charge clouds of the events, such as event 115 under first order side wall pixel 62 generated near the boundary between pixels 62 and 130, move along field line 116 and are collected by anode 130 that is adjacent to anode 62.

A similar situation exists, for example, for the second order sidewall pixel 130, but with a reduced effect relative to first order sidewall pixel 62. The electrons in the charge clouds of the events, such as event 117 under second order sidewall pixel 130 generated near the center of pixel 130, move along field line 118 and are collected by anode 130. The electrons in the charge clouds of the events, such as events 146 and 144 generated under second order sidewall pixel 130 closer to the boundary 142 between pixels 130 and 132, move along field line 120 and 121 and are collected by anode 130. The electrons in the charge clouds of the events, such as event 123 under second order side wall pixel 130 generated very close to the boundary 142 between pixels 130 and 132, move along field line 122 and are collected by anode 132 that is adjacent to anode 130.

An event is generated by photon absorption of radiation impinging on cathode 64 of detector 110 and absorbed in bulk 66. The photon absorption creates charge clouds of electrons and holes. The electron charge cloud is drifted toward the positive anodes and the hole charge cloud is drifted toward negative cathode 64. FIG. 5 is a schematic illustration for detector 110 made of CZT bulk 66 in which the lifetime (t)—mobility ($\mu$) product ($\mu$t) of the holes is low. Accordingly, the holes may recombine before moving a significant distance. In such a case, the contribution of the holes to the signal measured on the anodes is negligible, and, thus, the movement of the holes is not illustrated in FIG. 5 for clarity and ease of illustration.

The electrons in the charge clouds of the events are shown as drifted along trajectories 112, 114, 116, 118, 120, and 122 toward anodes 62, 130 and 132 from cathode 64 where events 111, 113, 115, 117 146 and 123 are generated at coordinate Z (140) where $Z=Z_0=0$, respectively. However, it should be noted that the events, such as event 144 having a cloud of electrons that is drifted along trajectory 121, may be generated by photon absorption at any point in the voxels corresponding to the pixels in bulk 66.

Accordingly, events may be generated at a certain voxel at any point in the range between boundary lines 142 between the voxels and along coordinate X indicated by reference numeral 138. Similarly, events may be generated at a certain voxel at any point in the range between cathode 64 and the anodes and along coordinate Z indicated by reference numeral 140.

For example, electrical field line 121, which is the trajectory line along which the charge cloud of the electrons, of event 144, is drifted toward anode 130. Event 144 is generated along coordinate X (138) in the vicinity of boundary line 142 and deep in bulk 66 along coordinate Z at point $Z(140)=Z_1$ close to anode 130.

Accordingly, it may be seen that part of the events, such as event 111, generated under first order sidewall pixel 62, are collected by anode 62, and the other part of the events, such as events 113 and 115, generated under first order sidewall pixel 62 migrate to second order sidewall pixel 130, and are collected there by anode 130 adjacent to anode 62. Similarly, part of the events generated under second order sidewall pixel 130, such as events 117, 144 and 146, are collected by anode 130, and the other part of the events, such as event 123, generated near boundary line 142 between the voxels corresponding to pixels 130 and 132 and under second order sidewall pixel 130 migrate to inland pixel 132 and are collected there by anode 132 adjacent to anode 130. It may be noted that the fraction of events migrating from first order sidewall pixel 62 to its adjacent pixel, i.e., second order sidewall pixel 130, is larger than the fraction of events migrates from second order sidewall pixel 130 to its adjacent pixel, i.e., inland pixel 132.

An analysis performed on thousands of wafers compared the average number of events detected per unit area in two types of samples. The first type was wafers with regions, such as portions 15 of FIG. 2, having their sidewalls 40 left as they are after dicing. The second type was wafers with similar portions 15 and sidewalls 40, but with the sidewalls polished after dicing, and with insulating tape with conductive strips applied on these sidewalls, as discussed in U.S. Pat. Nos. 6,034,373 and 5,905,264.

The comparison showed that the same average number of events per unit area was detected for both types of the wafers. However, the performance (e.g., sensitivity) of the first order sidewall pixels, such as, pixels 62 of FIG. 5 in the samples with no wall treatment after dicing were significantly inferior to those of the first order sidewall pixels in the samples that have sidewall treatment. Due to the migration of events toward the interior of the detector, the performance of the second order sidewall pixels, such as, pixels 130 of FIG. 5 and their adjacent inland pixels, such as pixels 132, in the samples with no wall treatment after dicing were found significantly superior to those of the second order sidewall pixels and their adjacent inland pixels in the samples that have sidewall treatment.

As a result, in both types of samples (detectors), either when sidewalls 40 are with or without treatment (e.g., polishing and taping) after dicing, they still have the same average number of events per unit area thus, there is the same amount of event loss in both types. The reason for the difference between the performance of the sidewall pixels and their adjacent inland pixels is because of the event migration from the first order sidewalls pixels to the second order sidewall pixels and from the second order sidewall pixels to their adjacent inland pixels. Accordingly, both types of the detectors have the same average sensitivity and they differ only by the event distribution between their pixels.

Since the events loss is the same for both types of the detectors (the first type with no treatment to sidewalls 68 (FIG. 5) after dicing, and the second type with treatment to walls 68 after dicing), equalizing the performance of both types of the detector may be done in various embodiments by electronic correction to the events distribution in the detector type with no treatment to its sidewalls. The purpose of the electronic corrections is to assign the events that are generated in one pixel and migrate to another pixel back to the pixel where these events were generated.

In various embodiments, the electronic corrections include the following: First, an event is collected by one of the pixels 16 of FIG. 2. Next, it is identified under which of the pixels 16 the event was generated. Then, if the pixel 16 that collects the event is the same as the pixel 16 under which the event was generated, it means that there is no event migration from one pixel to another and the event is counted in this same pixel 16. However, if the pixel 16 that collects the event is different from the pixel 16 under which the event was generated, there is event migration from one pixel to another and the event is counted in pixel 16 under which the event was generated.

It may be noted that the electronic corrections in various embodiments are not limited only to first and second order sidewall pixels and corner pixels 34, 36 and 32 (FIG. 2), respectively. For example, these electronic corrections may be applied to all pixels 16 in order to electronically correct the performances of bad inland pixels as well to increase production yield. A more detailed explanation for the electronic corrections for first, second, and third order sidewall pixels is provided below, as well as a more detailed explanation of the electronic corrections for improving the performance of bad inland pixels.

First, conventional primary and secondary (non-collected induced) signals are discussed. In various embodiments, the electronic corrections are based on mixed primary and mixed secondary (non-collected induced) signals. First, conventional primary and secondary (non-collected induced) signals are discussed. A conventional primary signal is the signal produced on an anode of a pixel, such as pixel anode 130 of FIG. 5, under which a corresponding event 144 is produced. In a case of a conventional primary signal, the electrical charge of the event 144 is collected by the same anode 130 under which event 144 was produced. A conventional secondary (non-collected induced) signal is the signal produced by the primary event on the anode(s) of a pixel, such as pixels 132 and 62, that is adjacent to pixel 130, in which event 144 is produced and collected. The conventional non-collected induced signals may also be referred to as conventional secondary signals.

The conventional secondary (non-collected induced) signals on the anodes of pixels 132 and 62 that are adjacent to pixel 130 are produced by induction without the electrical charge of event 144 being collected there. Non-collected induced signals may also be referred to as secondary signals herein.

To better understand the electronic corrections, reference is first made to known conventional primary and secondary signals, as described above, related to events 144 and 146 produced in primary pixel 130 and measured in pixels 130, 132 and 62. In this discussion FIGS. 5 and 6 will be alternatively referred to.

Figure 6:
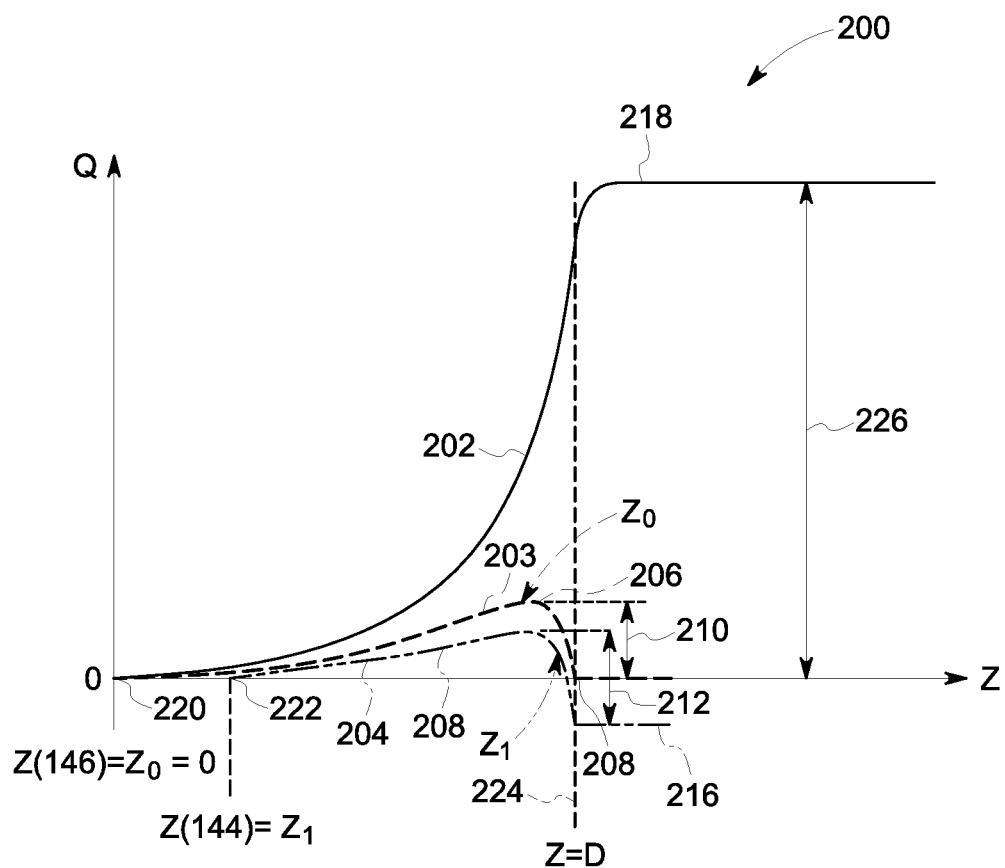
FIG. 6 is a schematic illustration of a graph showing a conventional primary signal and conventional secondary signals.

FIG. 6 is a schematic illustration of a graph 200 showing a conventional primary signal 202 of a pixel 130 (see also FIG. 5) and conventional secondary signals 203 and 204 measured on pixels 132 and 62 for events 146 and 144 generated and collected in pixel 130, respectively. Curves 202, 203, and 204 in graph 200 are the charge Q measured in pixels 130, 132, and 62 as a function of the value of coordinate Z along which the charge clouds of events 146 and 144 are drifted toward anode 130 from the points $Z(146)=0$ and $Z(144)=Z_1$ were they are generated, respectively.

Conventional primary signal 202 is substantially the same for events 144 and 146, since in the example the aspect ratio between anode 130 and the thickness D (148) of detector 110 is small and produces a strong "small pixel" effect. In such a case, the conventional primary signal substantially does not depend on the depth of interaction (DOI) of events 144 and 146, and thus, the graph 202 of the conventional primary signal in pixel 130 is substantially the same for events 144 and 146 in pixel 130 even though these events were generated in different locations (DOI) along coordinate Z (140).

Conventional secondary signals 203 and 204 are non-collected induced signals in pixels 132 and 62 for events 146 and 144 generated on cathode 64 at point $Z(146)=Z_0=0$ and deep in bulk 66 at point $Z(144)=Z_1$, respectively. Accordingly curves 203 and 204 start at points $Z(146)=0$ and $Z(144)=Z_1$, respectively.

Curve 202 of the conventional primary signal of events 144 and 146 generated and measured in pixel 130 starts at point 220 where $Z(146)=Z_0=0$ and reaches a maximum value of Q at positive flat value 218 and stays there. The maximum amplitude value 226 of curve 202 is measured between the value of the maximum positive plateau 218 and the zero value ($Q=0$).

Curve 203 of the conventional secondary signal of event 146 generated in pixel 130 and measured in pixels 132 starts at point 220 where $Z(146)=Z_0=0$ and reaches a maximum value of Q at positive peak 206 and then goes down to a final flat value 214, which is equal to $Q=0$. The maximum amplitude value 210 of curve 203 is measured between the value of the maximum positive peak 206 and the final flat value 214($Q=0$).

Curve 204 of the conventional secondary signal of event 144 generated in pixel 130 and measured in pixel 132 starts at point 222 where $Z(144)=Z_1$ and reaches a maximum value of Q at positive peak 208 and then goes down to a final flat negative value 216, which is negative and equals to $Q<0$. The maximum amplitude value 212 of curve 204 is measured between the value of the maximum positive peak 208 and the final flat negative value 216 ($Q<0$).

The maximum amplitude value 226 of the conventional primary signal in pixel 130 illustrated by curve 202 depends relatively weakly on the coordinates (X, Z) in pixel 130. However, the maximum amplitude values 210 and 212 of the secondary signals in pixel 132 corresponding to events 146 and 144 that are illustrated by curves 203 and 204, respectively, depend more significantly on the coordinate X (138) where events 146 and 144 are generated in pixel 130. Generally, the closer the event to the boundary between adjacent pixels, such as, boundary 142 between primary pixel 130 and secondary pixel 132, the larger are the values of the maximum amplitudes 210 and 212.

The largest value of the maximum amplitudes, such as, maximum amplitudes 210 and 212 of the conventional secondary signals, have been found to reach a value up to about only 15% of the value of the conventional primary signal when the event is very close to boundary 142 between pixels 130 and 132. Further, it was found that even this value of 15% of the primary signal is achievable for the maximum amplitudes only when using a slow shaper for the primary signal and a fast shaper for the secondary signal (e.g., as disclosed by U.S. Pat. No. 9,632,186). It may be noted that the dependency of the location of the event relatively to the boundary may be used, for example, to derive the coordinates X (138) and Z (140) of the event location of events, such as, events 146 and 144 inside pixel 130 of radiation detector 110, as disclosed in U.S. Pat. Nos. 10,324,202 and 10,481,285.

It may further be noted that the final plateau values 214 and 216 of the conventional secondary signals in pixel 132 corresponding to events 146 and 144 that are illustrated by curves 203 and 204, significantly depend on the DOI, which is the coordinate Z (140) in pixel 130 where events 146 and 144 are generated. Further, curves 202, 203, and 204 all reach their final values when the events, such as events 144 and 146, are collected in the primary pixel 130 at Z (224) that is equal to the thickness D of the detector. This dependency may be used, for example, to derive the value of coordinate Z, which is the DOI of events, such as, events 146 and 144 inside pixel 130 of radiation detector 110, as disclosed in U.S. Pat. No. 10,481,285.

Next, unconventional primary and secondary signals as disclosed herein are discussed. The primary and the secondary signals used in the present disclosure are different from the conventional primary and the conventional secondary signals previously discussed in connection with FIG. 6. As explained above, a conventional primary signal is a signal measured in a primary pixel where the event is generated and also collected, and a conventional secondary signal is a signal measured in a secondary (non-collecting) pixel that is adjacent to the pixel where the primary signal is measured.

In contrast, certain primary and secondary signals according to the present disclosure result from a mixture of conventional primary and conventional secondary signals. Accordingly, they will be referred to herein as "mixed primary" and "mixed secondary" signals.

More specifically, in various embodiments, the mixed primary signal is a signal that starts as a conventional secondary signal and ends as a conventional primary signal. This means that the event is generated in a pixel that is not the mixed primary pixel, which is close (adjacent or nearby) to the mixed primary pixel and is collected by the mixed primary pixel. Thus, the event is generated at a mixed secondary pixel, that is close to the mixed primary pixel, and is collected by the mixed primary pixel, after migrating from the mixed secondary pixel to the mixed primary pixel.

Also, in various embodiments, the mixed secondary signal is a signal that starts as conventional primary signal and ends as conventional secondary signal. This means that the event is generated in the mixed secondary pixel and is collected by another pixel, which is the mixed primary pixel. This means that the event is generated at a mixed secondary pixel, that is close to the mixed primary pixel, and is collected by another pixel (i.e., the mixed primary pixel), after migrating from the mixed secondary pixel to the mixed primary pixel.

It may be noted that while conventional primary and secondary signals correspond to two immediately adjacent pixels, the mixed primary and the mixed secondary signals may corresponding to immediately adjacent pixels or pixels that are separated apart, such as a first order sidewall pixel and a third order sidewall pixel.

Figure 7:
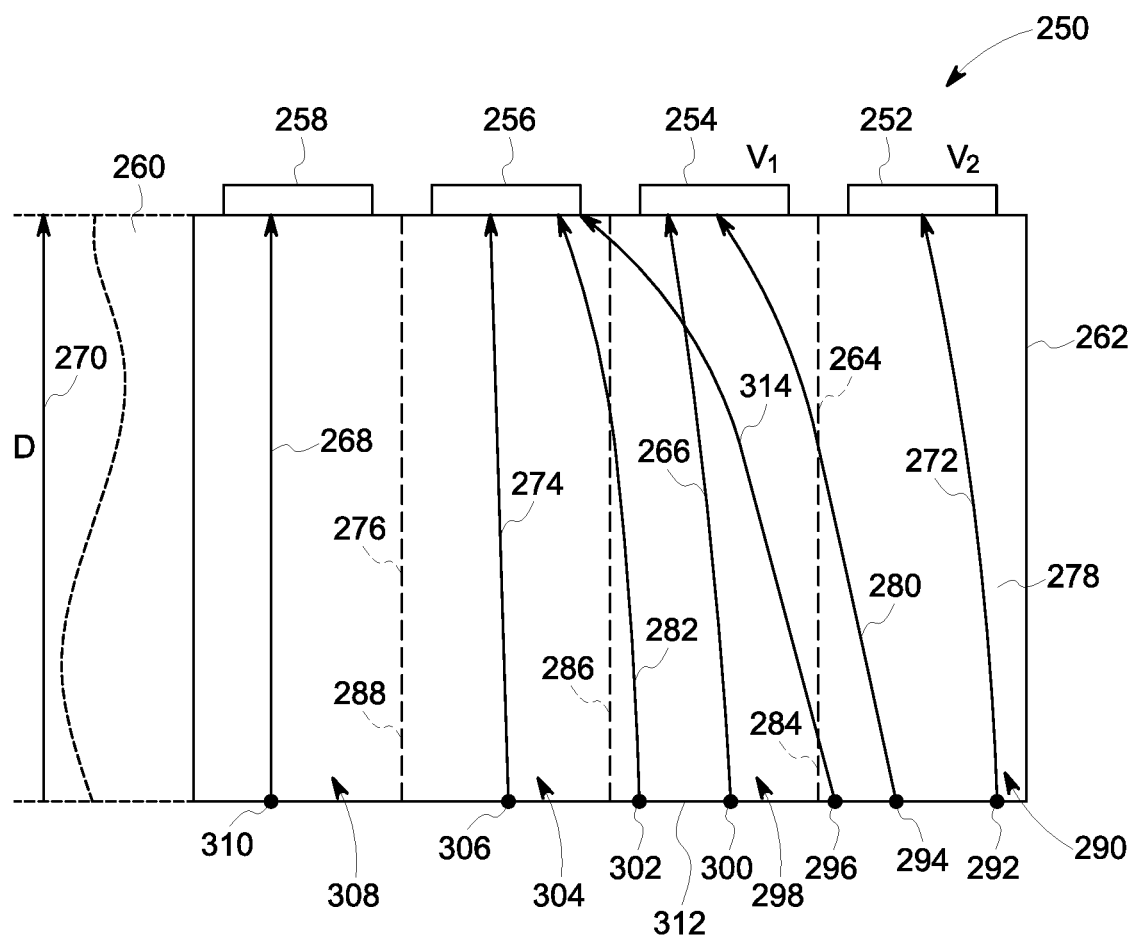
FIG. 7 is a schematic illustration of a radiation detector in accordance with various embodiments.
Figure 8:
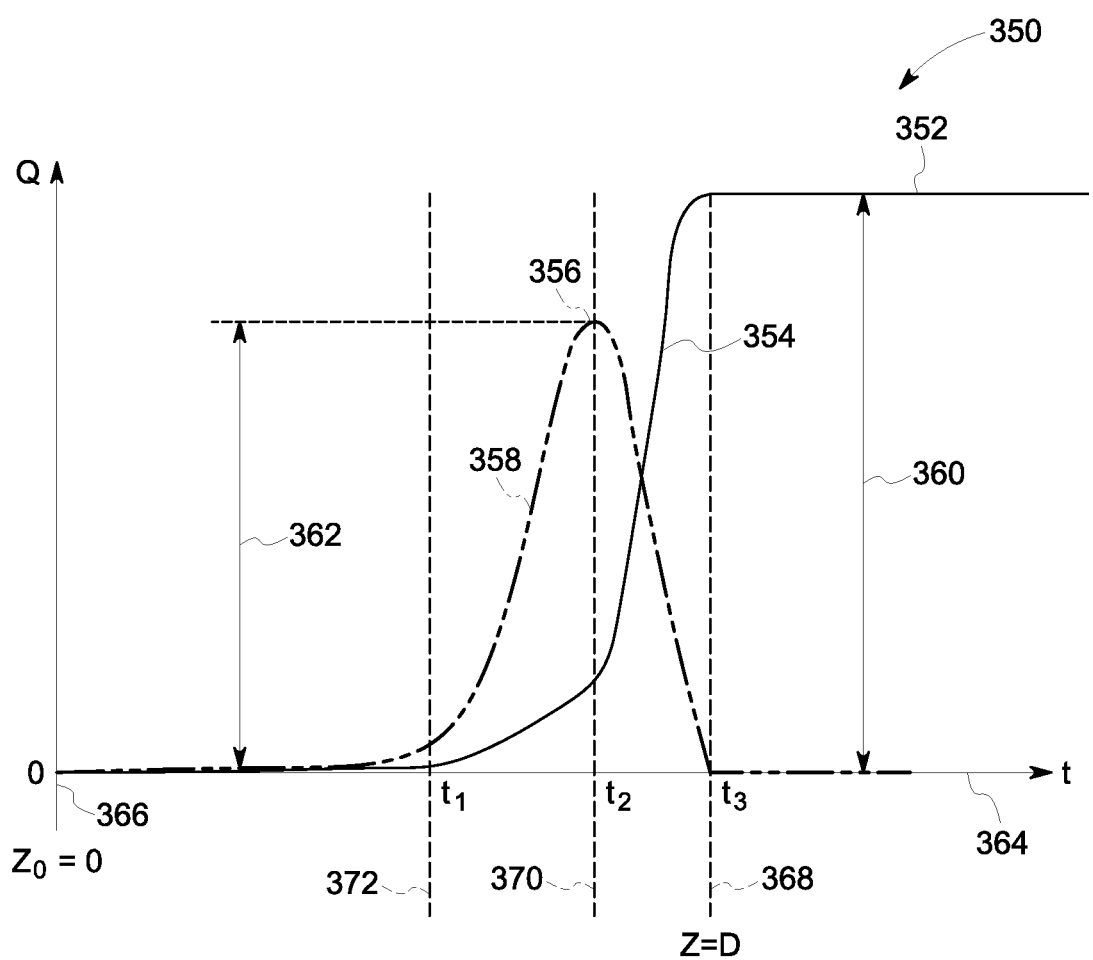
FIG. 8 schematically illustrates curves of a mixed primary signal and a mixed secondary signal for the radiation detector of FIG. 7.

Further explanation of the mixed primary and the mixed secondary signals will be provided in connection with FIGS. 7 and 8. FIG. 7 is a schematic illustration of a radiation detector 250 that is similar in various respects to radiation detector 110 of FIG. 5. It may be noted that the thickness D (270) of the detector 250 is significantly larger than the thickness D (148) of detector 10 and thus allows, as discussed below, migration of events from one pixel to another pixel which are not necessarily immediate adjacent but can be apart and separated, such as migration of events from first order sidewall pixels 252 to third order sidewall pixels 256. In addition, the large thickness D (270) may provide a relatively strong "small pixel effect." It may be noted that in the illustrated example, the paths 314 and 266 cross. In practice, paths or trajectories for a given detector operation/design would not cross (because the trajectories are defined by field lines that do not cross). Accordingly, it should be understood that the paths 314 and 266 correspond to different detector operation/design configurations.

Detector 250, similar to detector 110, includes sidewalls 262 that have similar sidewall effects to those discussed in connection with detector 110, which causes migration of events toward the interior of bulk 278 from sidewall pixels into more inward pixels. As mentioned above, these effects are caused by voltage $V_2$ on first order pixel 252 being lower than the voltage $V_1$ on the other pixels, sidewall interface between high dielectric constant in bulk 278 and lower dielectric constant in air, and larger number of charge attracting pixels on one side of the sidewall pixels.

As seen in FIG. 7, the depicted example detector 250 includes first order sidewall pixels 252, second order sidewall pixels 254, and third order sidewall pixels 256. Secord order and third order sidewall pixels 254 and 256 may receive events migrating from first order sidewall pixels 252. Third order sidewall pixels 256 may receive events migrated either from first order sidewall pixels 252 or second order sidewall pixels 254. Detector 250, unlike detector 110, includes third order sidewall pixels 256 that may receive events from first order sidewall pixels 252 since the thickness D (270) of the detector 250 is significantly larger than thickness D (148) of the detector 110, thus enabling migration of events from both first and second order sidewall pixels 252, 254 into third order sidewall pixels 256.

The depicted detector 250 also includes pixels 258, which are inland pixels, and which are relatively far away from the edges of detector 250 where the sidewalls 262 are located. Broken portion 260, illustrated by broken lines, illustrates that the sidewalls 262 are remote from the pixels 258. All the pixels of detector 250 are applied on the upper surface of semiconductor bulk-plate 278, and a monolithic cathode 312 is applied on the bottom surface of bulk-plate 278. Semiconductor bulk-plate 278 may be made from, for example, CZT. Voxels 290, 298, 304 and 308 inside bulk 278 are located under pixels 252, 254, 256 and 258, respectively. As seen in FIG. 7, a boundary is shown by a broken line 288 between adjacent voxels. The boundary line between voxels 290 and 298 is broken line 284, the boundary line between voxels 298 and 304 is broken line 286, and the boundary line between voxels 304 and 308 is broken line 276.

Events (or impacts or reception of photons) are also shown in FIG. 7. In the illustrated example, events 292, 300, 306 and 310 in corresponding voxels 290, 298, 304 and 308 under pixels 252, 254, 256 and 258 are generated close to the cathode 312 and move along trajectories 272, 266, 274 and 268, respectively. Each of the events 292, 300, 306, 310 starts, ends, and is collected in the same voxel under the same pixel where it started. This means that events 292, 300, 306 and 310 are conventional primary events that produce signals such as conventional primary signal 202 and conventional secondary signal 203 of FIG. 6.

Events 294 and 296, both in voxel 290 under pixel 252, are generated close to the cathode 312 and move along corresponding trajectories 280 and 314 from the cathode 312 under pixel 252 to the anodes of pixels 254 and 256, respectively, where they are collected. Event 302 in voxel 298 under pixel 254 is generated near cathode 312 and moves along trajectory 282 from the cathode 312 under pixel 254 to the anode of pixel 256 where it is collected.

Each one of the events 294, 296 and 302 is generated in a pixel that is different than the pixel where it is eventually collected. Accordingly, event 294 produces a mixed primary signal in second order sidewall pixel 254, where it is collected, and produces a mixed secondary signal in first order sidewall pixel 252, where it is generated. Also, event 296 produces a mixed primary signal in third order sidewall pixel 256 where it is collected, and produces a mixed secondary signal in first order sidewall pixel 252 where it is generated. Further, event 302 produces a mixed primary signal in third order sidewall pixel 256, where it is collected, and produces a mixed secondary signal in second order sidewall pixel 254, where it is generated.

FIG. 8 schematically shows a graph 350 including curve 354 of a mixed primary signal and curve 358 of a mixed secondary signal, showing the electrical charges developed on the anodes of the pixels of a radiation detector, such as detector 250 of FIG. 7, as a function of the time t. The signals of the depicted example curves 354 and 358 correspond to event 294 that is generated under first order sidewall pixel 252 and is collected by the anode of second order sidewall pixel 254, respectively. The mixed primary signal 354 is measured on the anode of second order sidewall pixel 254 where event 294 is collected. The mixed secondary signal 358 is measured on the anode of first order sidewall pixel 252 where the event 294 is generated.

Signals 354 and 358 may be produced, for example, in a Charge Sensitive Amplifier (CSA), with a corresponding CSA connected to each one of the pixels of a detector, such as, radiation detector 250 of FIG. 7. The CSA for a given pixel can be a part of discrete electronics, or part of an electronic channel in an Application Specific Integration Circuit (ASIC) that includes many electronic channels each including a CSA. The CSA is electrically connected to one pixel of a detector, such as, detector 250.

Mixed secondary signal 358 is measured on first order sidewall pixel 252 and produced by event 294 that starts to move from cathode 312 along trajectory 280 under the anode of pixel 252. In the range between cathode 312 and point 264 where trajectory 280 crosses boundary 284 between voxels 290 and 298 of pixels 252 and 254, respectively, event 294 induces charges on anode 252 in a way similar to a conventional primary signal. As a conventional primary signal in the above mentioned range, the signal that starts at time t=0 when the event 294 starts to move from cathode 312 (Z=0), a very small amount of charge is induced due to the strong "small pixel effect" until it arrives, on trajectory 280, at $t_1$ (372), closer to the anode of pixel 252. At this time $t_1$ (372) and closer location to anode 252, the signal 358 on pixel 252 starts to rise relatively fast, as happens with a conventional primary signal. This rise of signal 358 continues until time $t_2$ (370) when event 294 on trajectory 280 crosses boundary 284 at point 264 (see also FIG. 7). From this time $t_2$ (FIG. 8) and point 264 (FIG. 7), the event 294 is moving under the adjacent pixel 254 and away from the anode of pixel 252, and thus induces negative charges on the anode of pixel 252, in a manner similar to a conventional secondary signal, causing the charge Q of signal 358 to decrease relatively quickly until it reaches a value Q=0 at time $t_3$ (368) when event 294 is collected by the anode of the pixel 254 at Z=D (270).

Accordingly, the mixed secondary signal curve 358 is a mixture of conventional primary and conventional secondary signals that has a maximum peak 356 at time $t_2$ (370). The mixed secondary signal curve 358 starts as a conventional primary signal until it reaches its peak 356 at time $t_2$ and then continues from its peak value 362 to its final value Q=0 as a conventional secondary signal.

The amplitude of the value 362 of peak 356 of curve 358 of the mixed secondary signal was found to be much stronger than the amplitude 210 of a corresponding conventional secondary signal 203 shown in FIG. 6. In various embodiments, the amplitude 362 of the mixed secondary signal 358 in FIG. 8 that starts as a conventional primary signal may reach a value that is about 90% of the maximum value 218 of a corresponding primary signal 202 of FIG. 6, while the maximum value 210 of a conventional secondary signal 203 may be only about 15% of the maximum value 218 (amplitude 226) of the conventional primary signal 202 of FIG. 6. Accordingly, the mixed secondary signal 358 is much easier to detect and has a much better Signal to Noise Ratio (SNR) than the conventional secondary signal 203.

The mixed primary signal 354 is measured on the second order sidewall pixel 254 and produced by event 294 that starts to move from cathode 312 along trajectory 280 under the anode of pixel 252. In the range between cathode 312 and point 264 where the trajectory 280 crosses the boundary 284 between voxels 290 and 298 of pixels 252 and 254, respectively, the event 294 induces charges on the anode of pixel 254 in a way similar to a conventional secondary signal. As a conventional secondary signal in the above mentioned range, the signal starts at time t=0 when the event starts to move from cathode 312 (Z=0), inducing a very small amount of charges in pixel 254 because the event 294 is under adjacent pixel 252 away from anode 254 on which signal 354 is measured, and also due to the strong "small pixel effect." This weak induced charge continues until event 294 arrives, on trajectory 280, at $t_1$ (372), closer to the anode of pixel 254.

At this time and location the mixed primary signal 354 on pixel 254 starts to rise similar to a conventional secondary signal. This rise of signal 354 continues while event 294 continues to move closer to anode 254 and voxel 298 until time $t_2$ (370) when the event 294 on trajectory 280 crosses the boundary 284 at point 264 (see also FIG. 7). From this time $t_2$ (FIG. 8) and point 264 (FIG. 7), the event 294 moves in voxel 298 toward and under the anode of pixel 254, thus quickly inducing charge on this anode, in a manner similar to a conventional primary signal. The transition of the mixed primary signal 354 from being similar to a conventional secondary signal to being similar to a conventional primary signal causes the change in the slope of the mixed primary signal curve 354 at $t_2$ (370). This process continues until event 294 is collected at time $t_3$ by the anode of pixel 254 at Z=D (368). From time $t_3$ and on, the charge stays on the integration feedback capacitor of the CSA to produce maximum plateau 352 of mixed primary signal 354.

Accordingly, the mixed primary signal corresponding to curve 354 is a mixture of conventional secondary and conventional primary signals that has a maximum plateau 352 at time $t_3$. The mixed primary signal 354 starts at t=0 as a conventional secondary signal until time $t_2$, and continues from $t_2$ as a conventional primary signal to its final maximum value 360 of plateau 352. The amplitude of the final maximum value 360 of plateau 352 of curve 354 of the mixed secondary signal was found to be similar to the amplitude 226 of plateau 218 of a corresponding conventional primary signal 202 shown in FIG. 6.

As seen in FIG. 7, first, second, and third order sidewalls pixels (e.g., pixels 252, 254 and 256), collect two types of events. A first type of events are conventional events that are generated under and collected by the same pixel, such as event 292 that is generated in voxel 290 of pixel 252 and is collected by the anode of the same pixel 252, event 300 that is generated in voxel 298 of pixel 254 and is collected by the anode of the same pixel 254, and event 306 that is generated in voxel 304 of pixel 256 and is collected by the anode of the same pixel 256.

When using a radiation detector, such as the detector 250 of FIG. 7, to acquire radiation emitted from an object (e.g., for reconstructing an image), this type of conventional events may be counted according to known techniques (e.g., assigning the events to the pixels where these events are measured and counting the number of events in the pixels where they are measured and generated).

The second type of events are migrating events that are generated under a first pixel and collected at a different, second pixel. For example, migrating events may originate under first and second orders sidewall pixels, such as pixels 252 and 254 of FIG. 7, but are detected in pixels that are different than the pixels where they are generated. Example migrating events from FIG. 7 include event 294 generated at voxel 290 of first order sidewall pixel 252 and collected by the anode of different pixel 254, event 296 generated at voxel 290 of first order sidewall pixel 252 and collected by the anode of different pixel 256, and event 302 generated at voxel 298 of second order sidewall pixel 254 and collected by the anode of different pixel 256.

Generally, for radiation imaging, events should be counted in pixels according to the pixel locations where the events are generated, or originate. For conventional (or non-migrating) events, the pixels that collect the events are the same pixels in which the events are generated. However, that is not the case for migrating events.

In order to assign the migrating events to the correct pixels (i.e., the pixels where the events are generated), the events should be identified to differentiate them from conventional events. Further, the pixels in which these events are generated, which are different than the pixels that detect the migrating events, should be identified. This is explained below with reference to FIGS. 7 and 8.

It may be noted that for conventional events 292, 300, and 306 there is one conventional primary signal per event that is measured on the same anode under which the event is generated. In contrast, for migrating events 294, 296 and 302 there are two signals per each event, with two signals appearing simultaneously and in coincidence on two different pixels. For example, event 294 simultaneously produces two coincident signals, namely one signal which is a mixed primary signal 354 on anode 254, and second signal that is a mixed secondary signal 358 on anode 252. Similarly, event 296 simultaneously produces two coincident signals, a first signal which is a mixed primary signal 354 on anode 256, and a second signal which is a mixed secondary signal 358 on anode 252. Also similarly, event 302 simultaneously produces two coincident signals—a mixed primary signal 354 on anode 256, and a mixed secondary signal 358 on anode 254. Accordingly, two coincident signals that appear simultaneously on two different anodes, especially if these anodes are included in the group of first, second, and third order sidewall pixels 252, 254 and 256, indicate that these coincident events are migrating events.

The mixed secondary signal 358 appears on the anode under which the event is generated. Accordingly, the anode with the mixed secondary signal corresponds to the pixel in which the event is counted for imaging purposes. There are two ways to identify which is the mixed secondary signal out of the two coincident signals including both the mixed primary and mixed secondary signals.

The first way is based on the fact that the mixed secondary signal of a certain event is weaker than the mixed primary signal of the same event. Accordingly, in a case for which two coincident signals appear simultaneously on two different anodes, indicating the existence of a migrating event, the pixel with the weaker signal out of the two coincident signals may be understood as the pixel in which the migrating event is generated, and the event may be counted in that pixel.

The second way is based on the fact that the mixed secondary signal of a certain event appears closer to the sidewall 262 than the mixed primary signal of the same event, since the mixed secondary signal appears in the pixel where the event is generated and from there the event migrates inward into the bulk 278, and farther from the sidewall 262 where the mixed primary signal is produced. Accordingly, for a case in which the two coincident signals appear simultaneously on two different anodes, indicating the existence of a migrating event, the pixel closer to sidewalls 262 having one signal out of the two coincident signals may be understood as the pixel in which the migrating event is generated, and the event may be counted in that pixel.

However, it may be noted that two simultaneous signals may appear on two different pixels for a case of charge sharing between two adjacent pixels as well. Charge sharing occurs when an event is generated on boundary lines, such as boundary lines 276 between pixels, and thus the event may be assigned to either pixel. Charge sharing correction may be performed by summing the energy (charge) values of the shared events.

In various embodiments, to help ensure that conventional events will produce only one signal per event, the threshold level of electronic channels connected to the pixels may be set to a predetermined threshold, for example above 15% of the maximum value of the conventional primary signal. In this situation the electronic channels block the conventional secondary signals, which as explained above, are below the threshold level, and thus, for conventional events, only one signal will be produced per event, namely the conventional primary signal. The threshold in various embodiments is set so that all signal discussed herein other than conventional secondary signals are measured by the electronic system Accordingly, the conventional primary signal, the mixed primary signal, and the mixed secondary signal have amplitudes above the threshold level and are measured by the electronic system.

In a situation where the migrated events can be identified and assigned to be counted in the correct pixels, where they are generated, the events in detector portion 15 of FIG. 2 having untreated diced sidewalls 40 can be redistributed to be accurately identified at the locations where they are generated. Accordingly, in various embodiments, detectors having portions 15 with untreated diced sidewalls may have performance similar to those of detectors using polished sidewalls and insulated tape with conductive strips.

Figure 9:
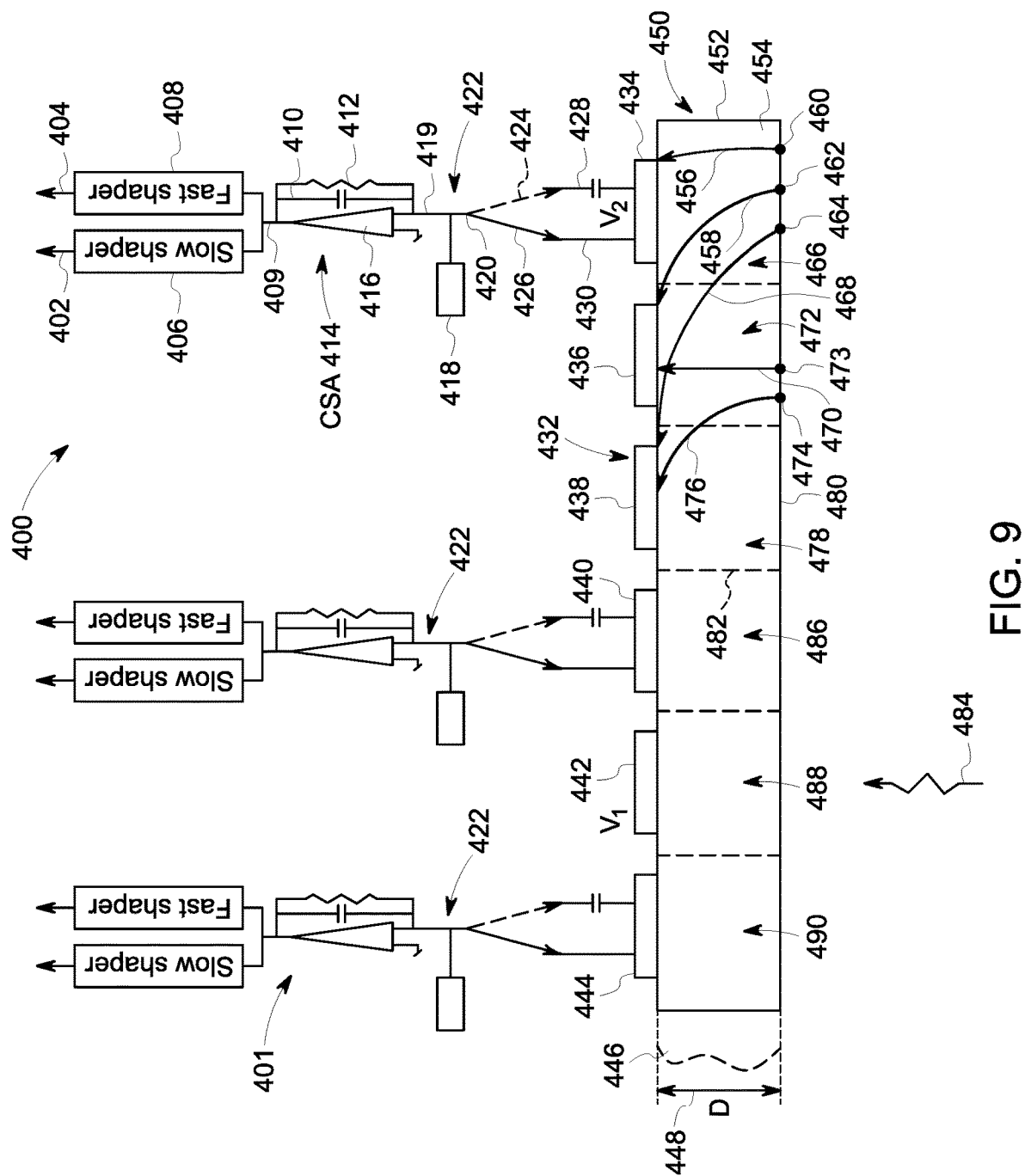
FIG. 9 is a schematic illustration of a radiation detector and associated electronics, in accordance with various embodiments.

FIG. 9 is a schematic illustration of a radiation detector assembly 400 integrated with electronics. The radiation detector assembly 400 is configured to perform techniques discussed herein for identifying migrating events and assigning those migrating events to the pixels where they are generated to be counted.

The depicted assembly 400 includes a radiation detector 450 and electronic channels 422 of application specific integrated circuit (ASIC) 401. The radiation detector 450 includes pixelated anodes 432 applied on the top surface of bulk plate 454. In the illustrated example, a monolithic cathode 480 is applied on the bottom surface of bulk 454. Each one of the electronic channels 422 is connected to one corresponding anode 432 of the detector 450. Each electronic channel 422 in the depicted example includes two subchannels, namely a slow subchannel 402, and a fast subchannel 404. The slow subchannel 402 includes a slow shaper 406, and the fast subchannel 404 includes a fast shaper 408. Subchannels 402 and 404 are connected to output 409 of CSA 414, that in turn includes operational amplifier 416, feedback capacitor 410, and feedback resistor 412. DC current compensator 418 is connected to input 419 of CSA 414. A switch (having two states in the illustrated example) 420 connects input 419 of CSA 414 to anodes 432 of the detector 450. The switch 420 has one state 426 (shown by a solid line) in which anodes 432 are directly connected by interconnections 430 to CSA's 414 in a DC coupling mode of operation, and a second state 424, shown by a broken line, which is not in use in FIG. 9. State 424 of the switch 420 connects CSA's 414 to anodes 432 of detector 450 via capacitor 428, and will be discussed below with reference to FIG. 11.

Each one of electronic channels 422 is electrically connected to a corresponding one of anodes 432, which are pixels 434, 436, 438, 440, 442, and 444 of detector 450. Pixels 434, 436 and 438 are first, second, and third order sidewall pixels, respectively. Broken portion 446 shown by a broken line indicates that detector 450 does not end at pixel 444 and that pixel 444 is remoted from the edges and sidewalls 452 of detector 450. The thickness of detector 450 is equal to D (448). It may be noted that while only 3 electronic channels 422 are shown for clarity and ease of illustration, each anode 432 may be connected to a corresponding electronic channel 422.

Voxels 466, 472, 478, 486, 488, and 490 are located under pixels 434, 436, 438, 440, 442 and 444 of detector 450, respectively. Each adjacent pair of voxels are separated by corresponding boundary lines (e.g., boundary line 482). Radiation 484 absorbed in the detector 450 at bulk 454 produces events. In the illustrated example, events 460, 462, and 464 are shown, as moving along trajectories 456, 458 and 468, respectively, in voxel 466 of first order sidewall pixel 434, and events 473 and 474 are shown, as moving along trajectories 470 and 476, respectively, in voxel 472 of second order sidewall pixel 436.

Events 460 and 473, in voxels 466 and 472, respectively, are conventional primary events. Events 460 and 473 are produced under first and second order sidewall pixels 434 and 436, respectively, and are collected by the same pixels 434 and 436 under which they were generated, respectively. Events 460 and 473 produce on pixels 434 and 436 conventional primary signals, such as signal 202 of FIG. 6, respectively. The amplitudes of conventional secondary signals, such as, signals 203 or 204 of FIG. 6 that events 460 and 473 produce on pixels 434 and 436 and 438, are below the threshold level of a comparator (not shown) in channels 422 thus, are not detected and measured. Alternatively, a lower threshold may be used for other purposes, such as charge sharing correction, and then induced charges having an amplitude that is lower than 15% of the primary signals (or other appropriate threshold) produced in the peak of the spectrum of the relevant isotope may be subsequently ignored.

Other events migrate from an original pixel under which they are generated to a different pixel under which they are collected. For example, events 462 and 464 in voxel 466 of first order sidewall pixel 434 are produced nearby cathode 480 under first order sidewall pixel 434, but then move and migrate from the pixel 434 to other pixels. Event 462 migrates from first order sidewall pixel 434 to second order sidewall pixel 436, is collected by second order sidewall pixel 436, and produces on pixel 436 a mixed primary signal, such as signal 354 of FIG. 8. Simultaneously, event 462 also produces on pixel 434 a mixed secondary signal, such as signal 358 of FIG. 8. Event 464 migrates from first order sidewall pixel 434 to third order sidewall pixel 438, is collected by third order sidewall pixel 438, and produces on pixel 438 a mixed primary signal, such as signal 354 of FIG. 8. Simultaneously, event 464 produces on pixel 434 a mixed secondary signal, such as signal 358 of FIG. 8. Event 474 migrates from second order sidewall pixel 436 to third order sidewall pixel 438, is collected by third order sidewall pixel 438, and produces on pixel 438 a mixed primary signal, such as signal 354 of FIG. 8. Simultaneously, event 474 produces on pixel 436 a mixed secondary signal, such as signal 358 of FIG. 8.

As mentioned above, the anodes 432 of the pixels of radiation deter 450 in FIG. 9 are electrically connected by interconnection switches 420 in state 426 to inputs 419 of CSA's 414 in a DC coupling mode. DC current compensators 418 null the leakage current of the detector at inputs 419 of CSA's 414 to avoid saturation of CSA's 414 due to the leakage current of the detector that charges feedback capacitor 410. Feedback capacitors 410 integrate the charge signals received from anodes 432 of detector 450 at inputs 419 of CSA's 414, and CSA's 414 output these signals at their outputs 409. CSA's 414 output signals at their outputs 409, such as conventional primary signals 202 of FIG. 6, mixed primary signals 354 of FIG. 8 or mixed secondary signals 358 of FIG. 8.

The signals from outputs 409 are received by subchannels 402 and 404. As further explained in U.S. Pat. No. 10,324,202, the subject matter of which is hereby incorporated by reference in its entirety, the slow shaper 406 in subchannel 402 acts as a bandpass filter that improves the SNR for conventional and mixed primary signals, such as signals 202 and 354 of FIGS. 6 and 8, respectively. The slow shaper 406 strongly attenuates mixed secondary signals, such as signals 358 of FIG. 8. The fast shaper 408 in subchannel 404 acts as a bandpass filter that improves the SNR for mixed secondary signals, such as signals 358 of FIG. 8.

Accordingly, for mixed secondary signals, such as signals 358 of FIG. 8, the electronic channel 422 produces, in its subchannel 404 (the fast subchannel), a signal that is stronger than the signal produced by its subchannel 402 (the slow subchannel). Thus, for example, event 462 produces a mixed secondary signal, such as signal 358 on pixel 434, and channel 422 connected to pixel 434 produces in its subchannel 404 a signal 358 that is stronger than signal 358 in subchannel 402. Simultaneously, event 462 produces a mixed primary signal that is measured on pixel 436 and produces in an electronic channel 422 connected to pixel 436 mixed primary signals in its subchannels 402 and 404.

Accordingly, when two signals are detected simultaneously and are in coincidence with two different pixels, the pixel, like pixel 434, with its fast subchannel 404 having a signal that is stronger than the signal in its slow subchannel 402, is the pixel where the event, like event 462, is generated. The other pixel, like pixel 436, collects the event, such event 462, and produces the mixed primary event signal in its slow and fast subchannels 402 and 404, respectively, when the signal for its corresponding slow subchannel 402 has better SNR and is the one that is measured and counted according to the location where it was generated. Such an event will thus be registered as happening in pixel 434, with the amplitude measured by pixel 436 with its subchannel 402.

It may be noted that $V_2$ represents the voltage between cathode 480 and the top surface of bulk 454 under first order sidewall pixel 434 that is calculated according to Eq. (1) above and $V_1$ represents the voltage between cathode 480 and the top surface of bulk 454 under inland pixel 442 that is calculated according to Eq. (4) above. $V_1$ and $V_2$ satisfy the mathematical relationships $V_1 > V_2$. It also may be noted, similar to the explanation above that accompanies FIG. 7, that in the illustrated example of FIG. 9, the paths 468 and 470 cross. In practice, paths or trajectories for a given detector operation/design would not cross (because the trajectories are defined by field lines that do not cross). Accordingly, it should be understood that the paths 468 and 470 correspond to different detector operation/design configurations.

Figure 10:
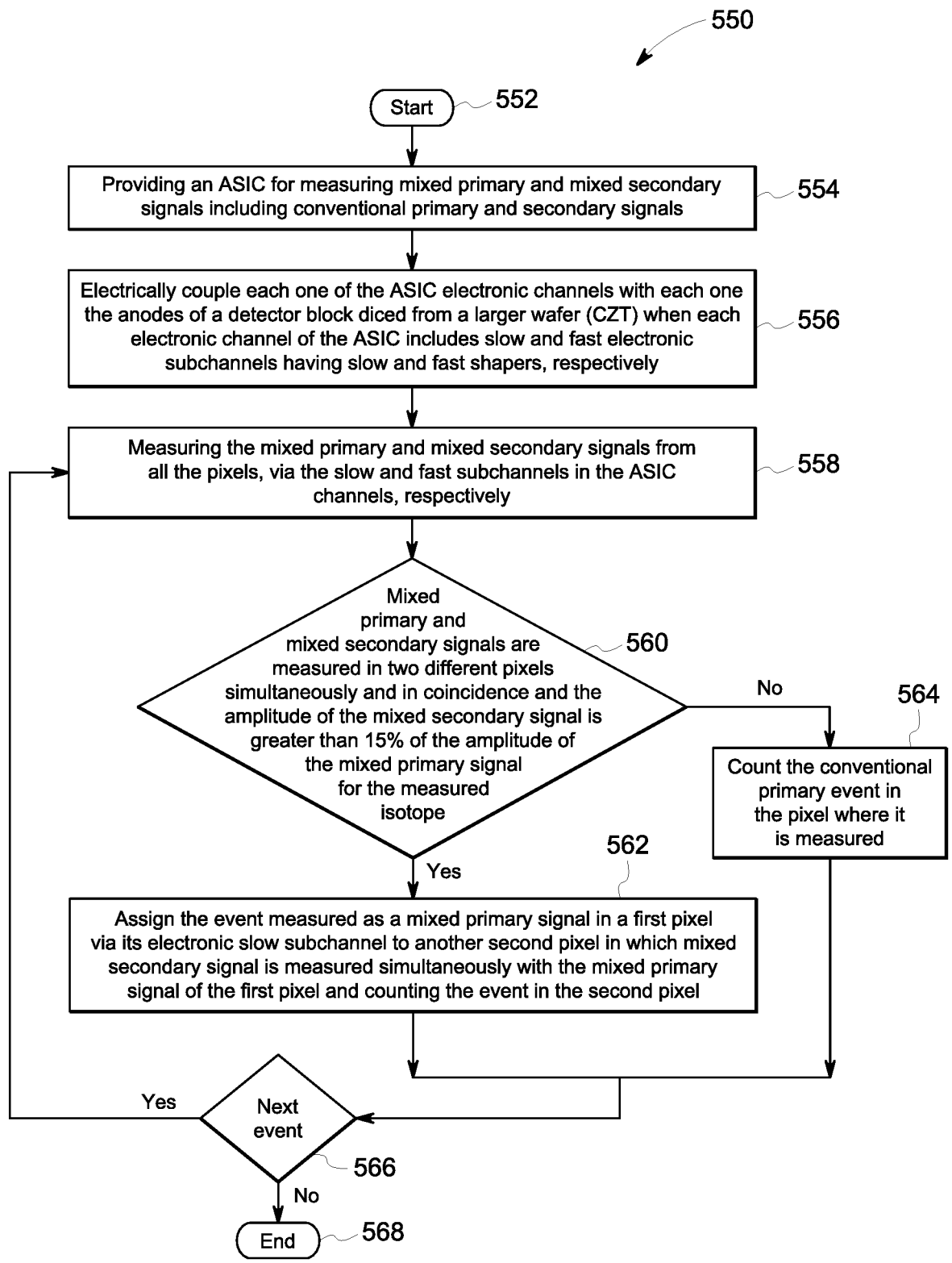
FIG. 10 provides a flowchart of a method in accordance with various embodiments.

FIG. 10 is a flowchart of a method 550 for reassigning and counting migrating events (462) in the pixels (434) where they are generated, while the mixed primary signals (354) of these migrating events (462) are measured in pixels (436) other than the pixels (434) where they are generated.

The method 550 starts at step 552, followed by step 554 in which ASIC (401) is provided for measuring mixed primary (354) and mixed secondary (358) signals (which as discussed herein are formed from portions of conventional primary (202) and secondary (203 or 204) signals. At step 556, each one of the ASIC's electronic channels (422) is electrically coupled to each one of the anodes (432) of a detector block (15) diced out from a larger wafer (CZT) (10). In the illustrated example, each electronic channel (422) of the ASIC (401) includes slow (402) and fast (404) electronic subchannels having slow (406) and fast (408) shapers, respectively.

At 558, the mixed primary (354) and mixed secondary (358) signals are measured from all the pixels (432), via the slow (402) and fast (404) subchannels in the corresponding ASIC channels (422). At Step 560, it is determined whether mixed primary (354) and mixed secondary (358) signals are measured in two different pixels (434) & (436) simultaneously and in coincidence, and the amplitude (362) of the mixed secondary signal (358) is greater than 15% (or other threshold) of the amplitude (360) of the mixed primary signal (354) for the measured isotope. If it is found that the criteria of step 560 are satisfied, then the method proceeds to step 562.

At step 562, the event (462) measured as a mixed primary signal (354) in a first pixel (436), via its electronic slow subchannel (402), is assigned to another second pixel (434) in which mixed secondary signal (358) is measured simultaneously with the mixed primary signal (354) of the first pixel (436), and the event (462) is counted in the second pixel (434) where it is generated instead of in the first pixel (436) despite the mixed primary signal (354) being measured in the first pixel (436).

If, however, all or part of the criteria mentioned in step 560 are not satisfied, then the method proceeds to step 564. At 564, the event (460) is measured as a conventional primary signal (202) in pixel (434) and is counted in the same pixel (434). After steps 562 or 564, it is determined at 566 whether there is a next event. If there is no next event, either migrating or conventional event, the process ends at step 566. If there is a next event, the process restarts with the next event from step 558.

Accordingly, various embodiments provide correction of event distribution, by assigning migrating events back into the pixels where they are generated, thus improving the performance of the sidewall pixels, which may be degraded by the unwanted effects of the sidewalls, such as untreated diced sidewalls 40 of detector block 15 in FIG. 2.

It may be noted that, when comparing the number of events measured in portion 15 of large wafer 10 of FIG. 1 to the number of events received in portion 15 of FIG. 2 after it is diced out from wafer 10, it may be seen that, for the same irradiation conditions, the number of events in portion 15 of FIG. 1 is similar to the number of events in portion 15 of FIG. 2 for two cases—a first case where the sidewalls 40 are left untreated after dicing and a second case where the sidewalls 40 are polished and isolated tape with conductive strip is applied on the sidewalls 40. However, in both cases (i.e., with or without walls treatment), the number of events in portion 15 of FIG. 2 after dicing is smaller than the number of events in portion 15 of FIG. 1 prior to the dicing. The reduction of the number of events after dicing is due to the recombination of the events' electrical charges in the vicinity of the walls caused by recombination centers in the vicinity of sidewalls 40 and surface recombination on sidewalls 40.

When the voltage $V_2$ of the first order sidewall pixel 434 is reduced significantly relative to $V_1$ of inland pixel 442 (FIG. 9), such that V1>>V2, all or most of the events generated in the first order sidewall pixel migrate out of pixel 434 away from walls 452 and into other pixels. This reduces the event recombination in the vicinity of walls 452. Accordingly, reducing $V_2$ by a significant enough amount brings the number of events in portion 15 of FIG. 2 having untreated sidewalls 40 to be substantially equal to the number of events in portion 15 of FIG. 1 prior to the dicing, when portion 15 of FIGS. 1 and 2 are irradiated under the same conditions.

It may be noted that, while reducing $V_2$ improves and preserves the sensitivity of region 15 in FIG. 1 to be equal to the sensitivity of region 15 in FIG. 2, it strongly deforms the events distribution (e.g., results in additional migration of events away from pixels under which they originate). However, the event distribution can be corrected by reassigning the location of the migrating events as described herein (e.g., in connection with FIGS. 5-10).

Figure 11:
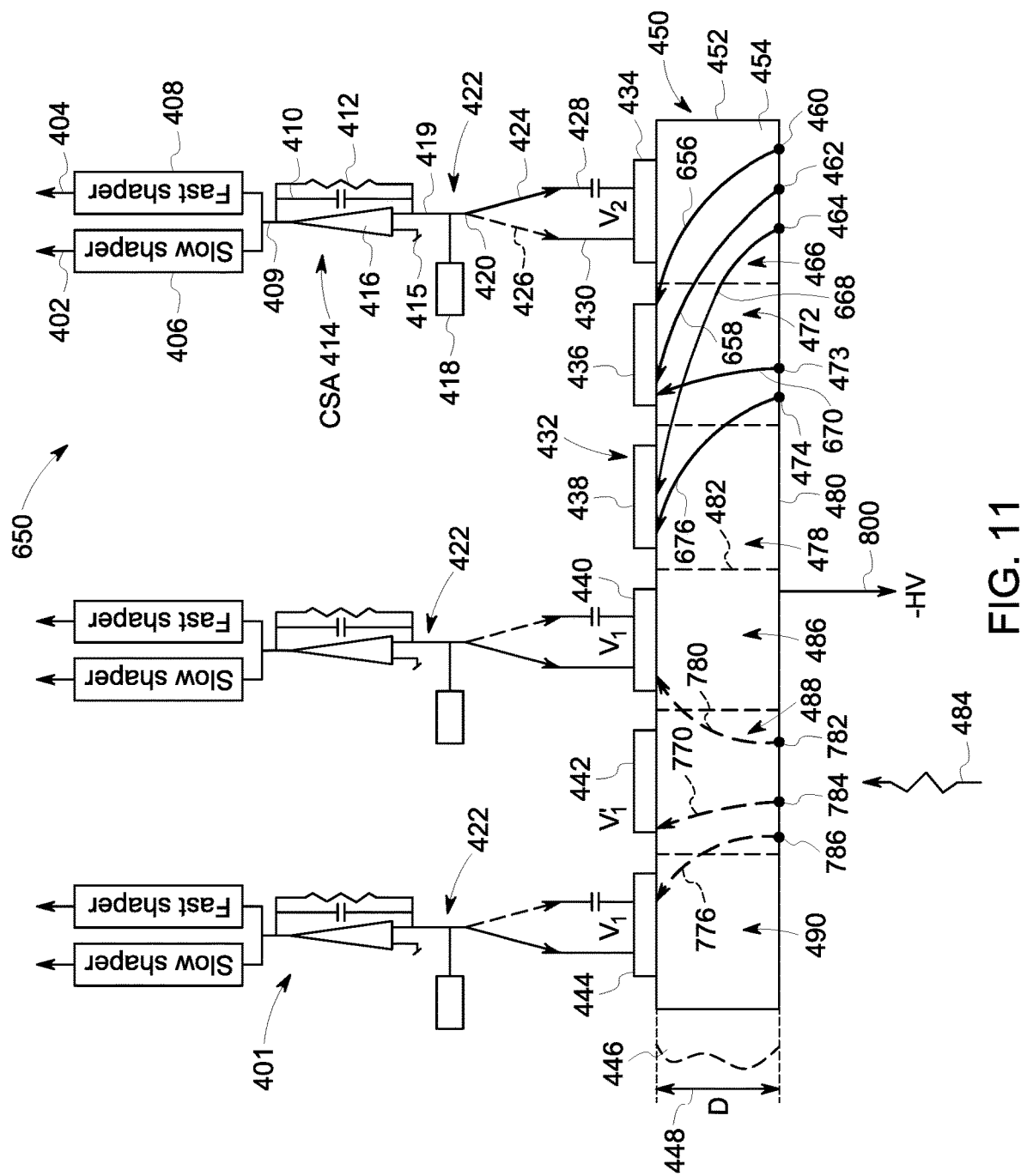
FIG. 11 is a schematic illustration of a radiation detector and associated electronics, in accordance with various embodiments.

FIG. 11 provides a schematic view of assembly 650 including a radiation detector 450 integrated with an ASIC 401 that is in certain respects generally similar to the assembly discussed in connection with FIG. 9. Accordingly, similar reference numerals are used to indicate similar parts and components in both FIGS. 9 and 11. The example embodiment of FIG. 11 provides for reduction of voltage $V_2$ and reassigning of migrating events back into the pixels where they are generated. In addition, the example embodiment of FIG. 11 provides for correction of event distributions of bad pixels, which may be utilized to improve the production yield of the radiation detectors (e.g., by allowing use of detector portions with relatively higher number of bad pixels).

FIG. 11 differs from FIG. 9 in that the connecting states of switches 420 of electronic channels 422, connected to the anodes of first order sidewall pixels 434, are changed from states 426 in FIG. 9 to be in state 424 (shown by a solid line in FIG. 11). The change in switch state causes the trajectories along which events 460, 462, 464, 473, and 474 are drifted toward anodes 432 of radiation detector 450 to change from trajectories 456, 458, 468, 470, and 476 in FIG. 9 to trajectories 656, 658, 668, 670, and 676, respectively in FIG. 11.

Inland pixel 442 is also represented different in FIG. 11. Whereas inland pixel 442 is a good inland pixel in FIG. 9, inland pixel 442 is a bad inland pixel in FIG. 11 due to high contact resistance $R_{CA}$ between the anode of pixel 442 and bulk 454 (see also FIG. 4). As can be seen from Eq. (4) above, increasing the anode contact resistance $R_{CA}$ in FIG. 11 causes reduction of voltage $V_1$ on bulk 454 under the anode of pixel 442 in FIG. 11, with the resulting voltage lower than $V_1$ on bulk 454 under the anode of pixel 442 in FIG. 9. The reduced voltage $V_1$ in FIG. 11 is marked as $V_1'$ and is also lower than $V_1$ corresponding to its neighbor pixels, such as pixels 440 and 444 in FIG. 11. In this situation, part of the events, such as, events 782 and 786 generated in voxel 488 under pixel 422, migrate along trajectories, such as, trajectories 780 and 776, to neighboring pixels, such as, pixels 440 and 444, respectively. Other events, such as, event 784 generated in voxel 488 under pixel 422, move along trajectories, such as trajectory 770, to be collected as conventional events by the anode of the same pixel 442 under which they are generated.

When switches 420 are connected, in state 424, via capacitors 428 to first order sidewall pixels 434, the coupling of the anodes of pixels 434 to electronic channels 422 of ASIC 401 is performed similar to the previously discussed AC coupling mode but, without a bleeding resistor that closes the electrical high voltage (−HV) DC loop of the detector 450. The bleeding resistor that does not exist in assembly 650 of FIG. 11 is usually connected, in conventional AC coupling, between input 419 and ground 415. Removing this bleeding resistor causes the desired reduction of $V_2$ in pixel 434, by the charging of capacitor 428.

Without the bleeding resistor, capacitor 428 is charged by the DC current (leakage current) of detector 450 to a voltage that is close to the voltage value of High Voltage (−HV) power supply 800. When the charging of capacitor 428 ends, the DC leakage current of detector 450 stops and the voltage on the anodes of first order sidewall pixels 434 is close to zero. In this situation the voltage $V_2$ on bulk 454 under the anodes of pixels 434 is also close to zero and satisfies $V_2 \ll V_1$. Under this condition, event migration out of pixel 434 is enhanced by the reduction of $V_2$. Accordingly, all or at least most of the events generated under first order sidewall pixels 434 in voxels 466, such as, events 460, 462, and 464, are attracted by the voltage $V_1$ on the pixels 432, such as pixels 436 and 438 that are neighbor pixels of pixels 434. Events, such as, events 460, 462, and 464, are drifted, along trajectories 656, 658, and 668, from pixels 434 into pixels 436 and 438 and away from walls 452.

When most of the events, like events 460, 462, and 464, are drifted away from the walls 452 and are collected by pixels, such as, pixels 436 and 438 they do not suffer from the recombination centers and the surface recombination associated with walls 452. Thus, after correcting the event distribution of the migrating events, as discussed herein, the sensitivity of first order sidewall pixels 434, such as first order sidewall pixels 34 in diced portion 15 of FIG. 2, is restored to be substantially equal to the sensitivity of inland pixels 432, such as the sensitivity in inland pixels 16 of FIG. 1, prior to the dicing of the walls of portion 15 of large wafer 10 in FIG. 1.

As explained above with reference to Eq. (4), a bad inland pixel 422 may have reduced sensitivity due to high anode or cathode contact resistance $R_{CA}$ or $R_{CC}$, respectively, that reduces voltage $V_1'$. When $V_1'$ on bulk 454 under the anode of inland pixel 442 is reduced, at least part of events such as events 782 and 786 generated in voxel 488 under pixel 442 migrate to another pixel such as pixels 440 and 444 that are adjacent to pixel 442. The event distribution of bad inland pixels like pixel 442, in which part of the events generated in pixel 442 are collected by other adjacent pixels like pixels 440 and 444, can be corrected using similar techniques to those discussed herein in connection with sidewall pixels.

When inland pixel 442 also includes defects, traps, and/or recombination centers like grain-boundaries and inclusions in its voxel 488, such defects can cause event loss in pixel 442. In such a case, enhancing the migration of events from pixel 442 to pixels 440 and 444, by setting the switch 420 of electronic channel 422 connected to pixel 442 into state 424, will increase the sensitivity of bad inland pixel 442 after its event distribution has been corrected for migrating events as explained herein.

The sensitivity of a bad pixel 442 may be improved by enhancing the migration of events out from pixel 442 and away from the problematic regions of voxel 442 and thus, reducing the loss of these events. The events like events 782 and 786 generated in pixel 442, migrate out of pixel 442 and are collected by pixels 440 and 444 are still counted as events of pixels 442 by detecting these events as discussed herein.

It should be noted that even though the voltage on first order sidewall pixels 434 and bad inland pixels 442 is close to zero when electronic channels 422 are connected to them via switches 420 that are in state 424, these pixels still produce mixed secondary signals due to the charge induction on the anodes of pixels 434 and 442 produced by the movement of the events (electron or charge clouds) under pixels 434 and 442 caused by the attraction of these events by the pixels that are adjacent to pixels 434 and 442. The mixed secondary signals are AC coupled from pixels 434 and 442 into electronic channels 422 by coupling capacitors 428. It also may be noted, similar to the explanation above that accompanies FIGS. 7 and 9, that in the illustrated example of FIG. 11, the paths 668 and 670 cross. In practice, paths or trajectories for a given detector operation/design would not cross (because the trajectories are defined by field lines that do not cross). Accordingly, it should be understood that the paths 668 and 670 correspond to different detector operation/design configurations.

Figure 12:
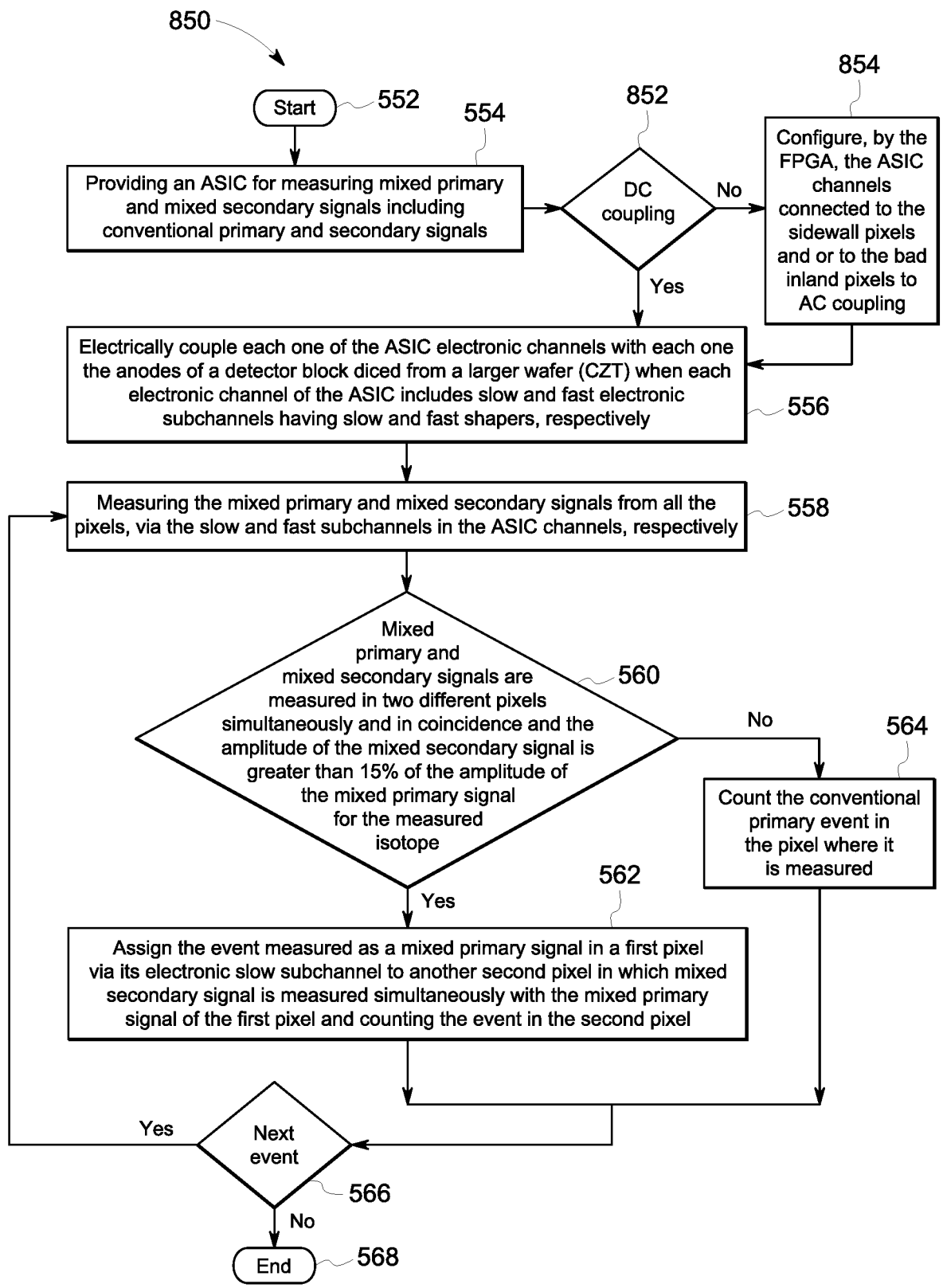
FIG. 12 provides a flowchart of a method in accordance with various embodiments.

FIG. 12 is a flowchart of a method 850. The method 850 may be used to reassign and count migrating events (462) in the pixels (434) where they are generated while the mixed primary signals (354) of these migrating events (462) are measured in pixels (436) other than the pixels (434) where they are generated.

Method 850 shares a number of generally similar steps with method 550. Accordingly, the same or similar steps in methods 550 and 850 of FIGS. 10 and 12, respectively, are indicated by the same reference numerals. The method 850 starts at step 552 followed by step 554 in which ASIC (401) is provided for measuring mixed primary (354) and mixed secondary (358) signals including conventional primary (202) and secondary (203 or 204) signals. In the illustrated example, all of the electronic channels (422) of ASIC 401 are set, by default configuration, to DC coupling with all switches 420 in state 426 configured for DC coupling. At step 852, it is determined whether DC coupling is needed for certain pixels. This decision may be made, for example, based on a pixels-map in which all the first order sidewall pixels (434) and the bad inland pixels (442) are indicated, based on a priori knowledge (e.g., based on position of sidewalls at a time of assembly and/or identification of bad pixels via testing). For at least part of the first order sidewall pixels (434) and the bad inland pixels (442) the decision made in step 852 is "No," and for the rest of the pixels the decision made in step 852 is "Yes". If the decision in step 852 is "Yes", the step that follows is step 556. If the decision in step 852 is "No", the step that follows is step 854.

At 854, a Field Programmable Gate Array (FPGA) receives the pixels-map, mentioned above, to configure the electronic channels (422) of ASIC (401) connected to the first order sidewall pixels (434) and or to the bad inland pixels (422) selected with decision "No" in step 852, to AC coupling in which switches 420 are in state 424.

This AC coupling enhances the migration of events (462) out of the pixels (434), which are AC coupled, but still allows the assignment of the events (462) back into the pixels where they are generated to be counted in these pixels (434). Step 556 follows step 854. From step 556 and on the processes of flowcharts 850 and 550 of FIGS. 10 and 12, respectively, are generally the same. As those steps are explained previously in connection with FIG. 10, the explanation will not be repeated here.

Accordingly, in various embodiments, detector portions (e.g., detector portions 15) may be produced having first, second and third order sidewalls pixels having substantially the same sensitivity as inland pixels 16 either of portion 15 of FIG. 1 or of FIG. 2. Maintaining the same sensitivity for sidewall pixels and inland pixels while the sidewalls are left as they are after dicing with no sidewall treatment allows very accurate tiling or butting of detector-blocks 15 of FIG. 2. This improved accuracy enables to maintain, very accurately, the pixel pitch between portions 15 and thus to improve the registration between the detector pixels and the openings of a corresponding collimator.

Figure 13:
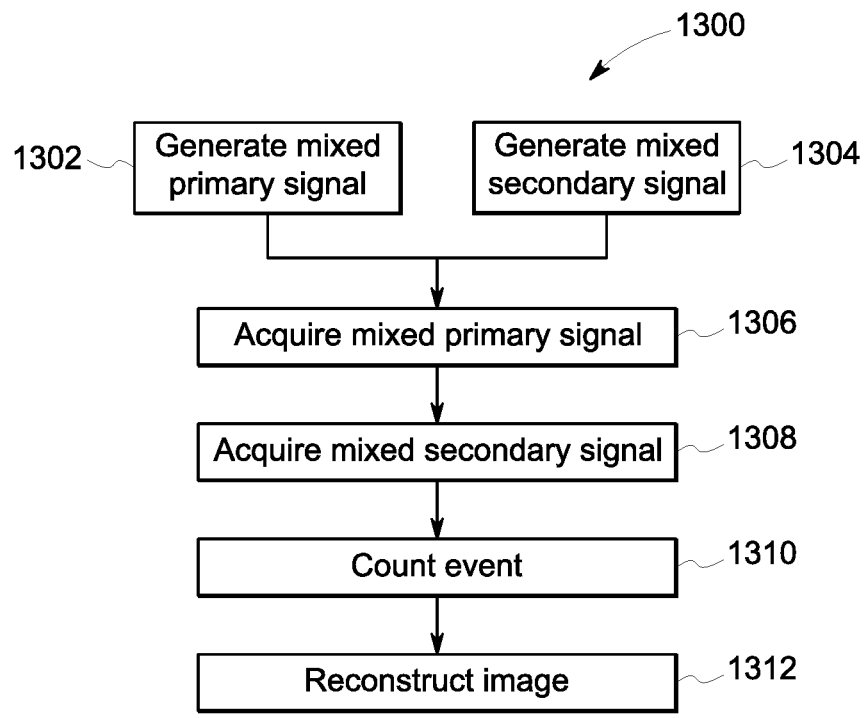
FIG. 13 provides a flowchart of a method in accordance with various embodiments.

FIG. 13 provides a flowchart of a method 1300 (e.g., for imaging), in accordance with various embodiments. The method 1300, for example, may employ or be performed by structures or aspects of various embodiments (e.g., systems and/or methods and/or process flows including those discussed in connection with FIGS. 10 and 12) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1300 may be able to be used as one or more algorithms to direct hardware (e.g., one or more aspects of the processing unit 53) to perform one or more operations described herein. The method 1300 may be utilized in connection with detector assemblies discussed herein, including those discussed in connection with FIGS. 2B, 9, and 11.

At 1302, a mixed primary signal is generated in at least one anode surrounding a pixelated anode that receives a photon. The mixed primary signal in the surrounding anode is generated responsive to reception of a photon by the pixelated anode. The surrounding anode may be immediately next to the receiving anode (e.g., a second order sidewall pixel generates a mixed primary signal responsive to reception by a first order sidewall pixel), or, as another example, the surrounding anode may be at a distance from the receiving anode (e.g., a third order sidewall pixel generates a mixed primary signal responsive to reception by a first order sidewall pixel). In various embodiments, the mixed primary signal starts as a conventional secondary signal and ends as a conventional primary signal in the collecting anode.

At 1304, a mixed secondary signal is generated responsive to the reception of the photon by the pixelated anode. The mixed secondary signal is generated by the pixelated anode under which the photon is originally received. Because the mixed primary signal at 1302 and the mixed secondary signal at 1304 are generated responsive to reception of the same photon, the signals are simultaneous or coincident. In various embodiments, the mixed secondary signal starts as a conventional primary signal and ends as a conventional secondary signal in the pixelated anode under which the photon is originally received.

At 1306, the mixed primary signal is acquired from a first pixelated anode (e.g., the surrounding anode at 1302). At 1308, the mixed secondary signal is acquired from a second pixelated anode (e.g., the receiving anode at 1302 and 1304).

At 1310, the event is counted for the second pixel responsive to receiving the mixed primary signal from the first pixelated anode and the mixed secondary signal from the second pixelated anode.

The steps 1302-1310 may be repeated for a number of events during an imaging process. Then, at 1312, an image is reconstructed using the counted events for each pixelated anode accumulated during the imaging.

Figure 14:
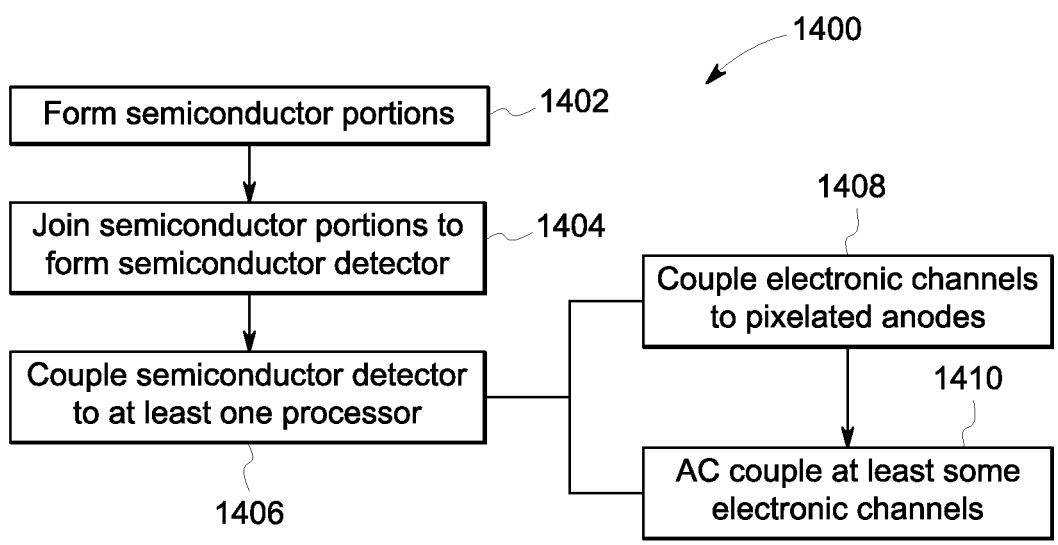
FIG. 14 provides a flowchart of a method in accordance with various embodiments.

FIG. 14 provides a flowchart of a method 1400 (e.g., for assembling a radiation detector assembly), in accordance with various embodiments. The method 1400, for example, may employ or be performed by structures or aspects of various embodiments (e.g., systems and/or methods and/or process flows including those discussed in connection with FIGS. 10 and 12) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. The method 1400 may be utilized in connection with detector assemblies discussed herein, including those discussed in connection with FIGS. 2B, 9, and 11.

At 1402, semiconductor portions (e.g., portions 15) are formed. For example, the semiconductor portions may be diced or cut from a larger semiconductor wafer, with the cut portions selected based on performance criteria, with the cut portions used to form a detector and the remaining portions discarded.

At 1404, the semiconductor portions are joined to form a semiconductor detector (see, e.g., FIG. 2B). For example, the semiconductor portions may be joined by tiling or butting them together. It should be noted that in various embodiments the sidewalls of the portions are not polished or taped prior to joining of the sidewalls.

At 1406, the semiconductor detector is coupled to at least one processor (e.g., processing unit 53 and/or electronics channels as discussed herein). The at least one processor is configured to acquire mixed primary and mixed secondary signals, and to count events as occurring in pixels for which mixed secondary signals are acquired.

At 1408, as part of coupling the semiconductor to the at least one processor, individual electronic channels of an ASIC are coupled to corresponding pixelated anodes. As discussed herein, each electronic channel may include a corresponding slow shaper (e.g., as part of a slow sub channel) and a fast shaper (e.g., as part of a fast sub channel).

In the illustrated embodiment, at 1410, at least some of the electronic channels are AC coupled to corresponding pixelated anodes (see, e.g., FIGS. 11 and 12 and related discussion). For example, first order sidewall pixels and/or bad pixels may be AC coupled based on a pixel formed using a priori knowledge of sidewall locations (based on tiling position of diced portions) and/or bad pixels.

Figure 15:
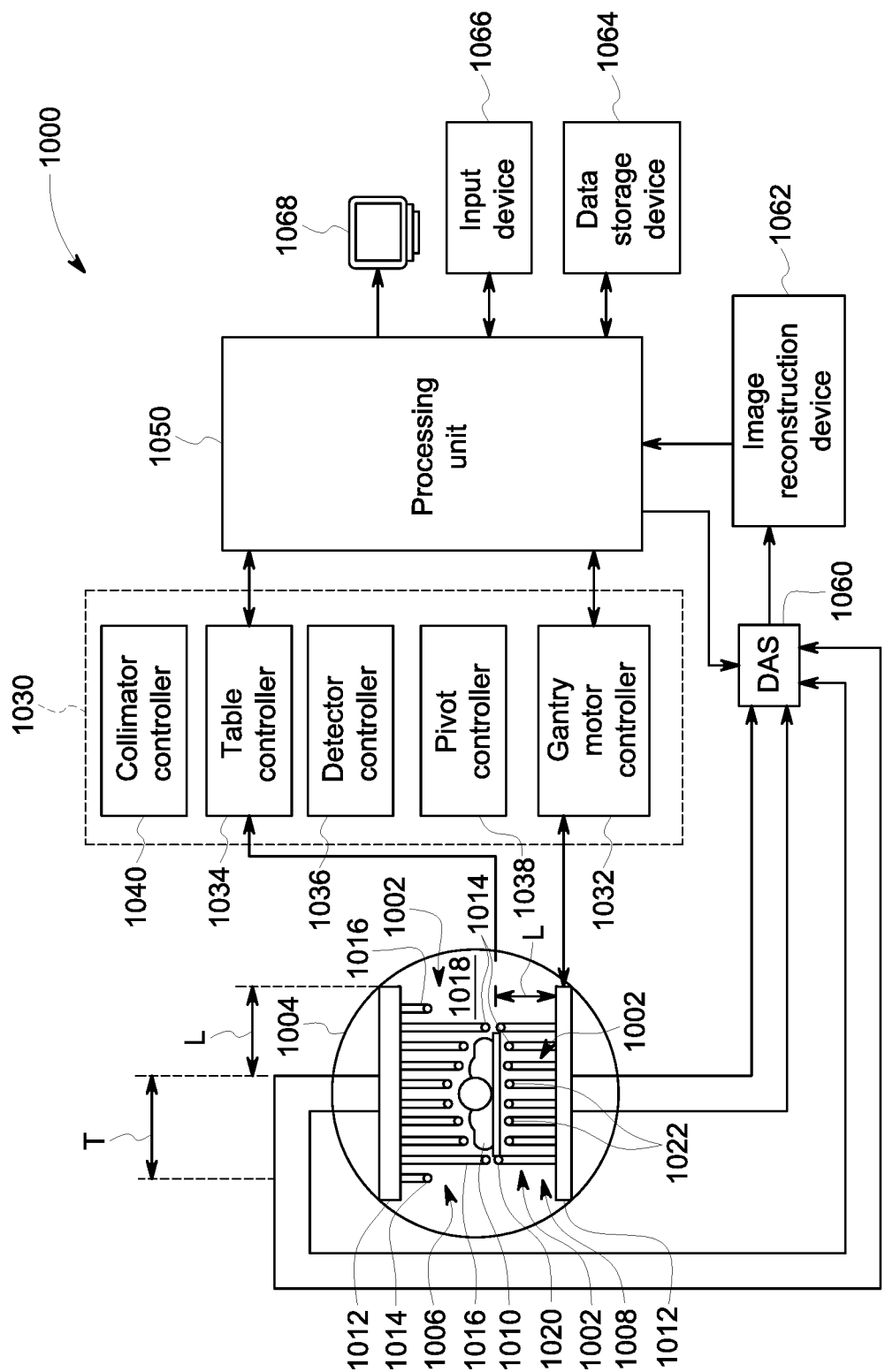
FIG. 15 provides a schematic view of an imaging system in accordance with various embodiments.

FIG. 15 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). In particular, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 15. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 15). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels. In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

In various embodiments, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially as described in more detail herein.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually as described in more detail herein. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 15). In various embodiments, the detector controller 1036 may control the detector carriers 1016 or the support members 1012 to move in different lateral directions. Detector controller 1036 may control the swiveling motion of detectors 1002 together with their collimators 1022.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 15 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

Figure 16:
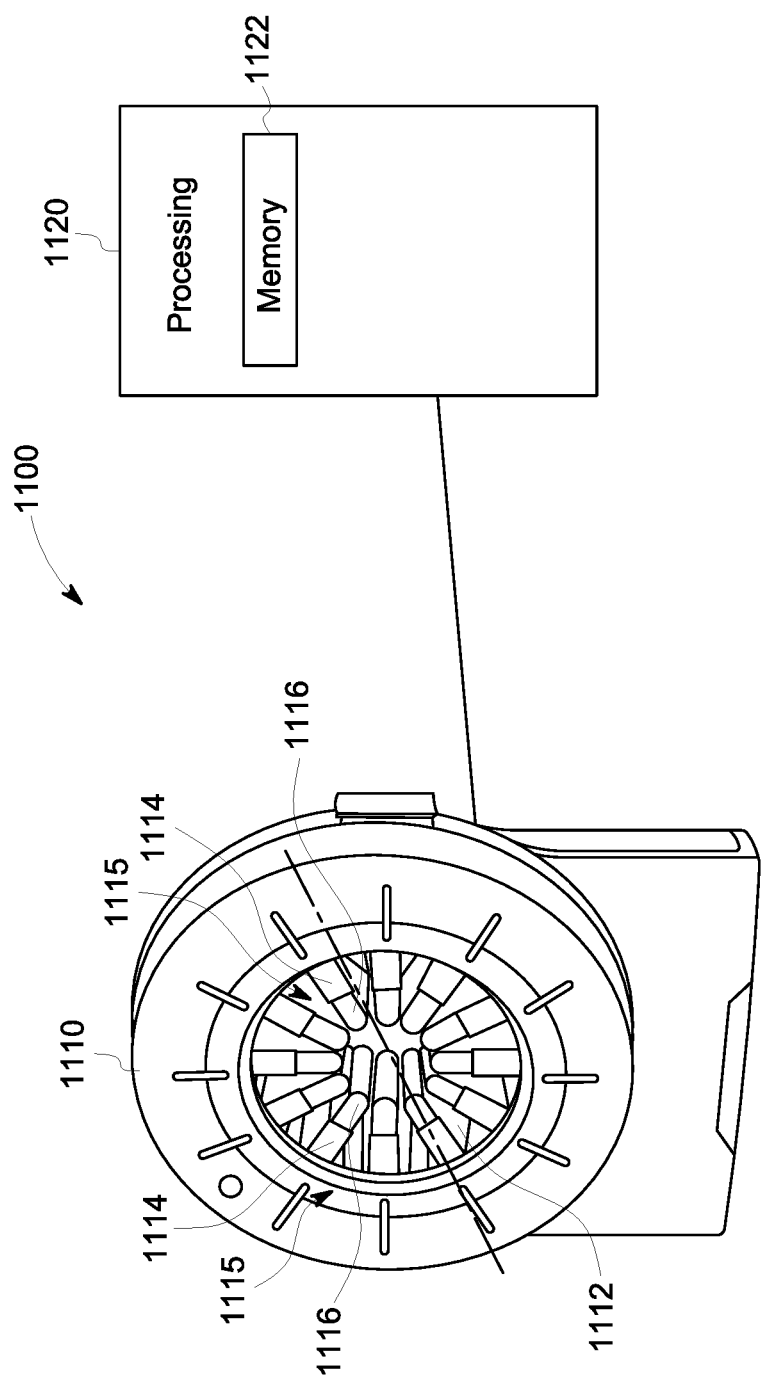
FIG. 16 provides a schematic view of an imaging system in accordance with various embodiments.

It may be noted that the embodiment of FIG. 15 may be understood as a linear arrangement of detector heads (e.g., utilizing detector units arranged in a row and extending parallel to one another. In other embodiments, a radial design may be employed. Radial designs, for example, may provide additional advantages in terms of efficiently imaging smaller objects, such as limbs, heads, or infants. FIG. 16 provides a schematic view of a nuclear medicine (NM) multi-head imaging system 1100 in accordance with various embodiments. Generally, the imaging system 1100 is configured to acquire imaging information (e.g., photon counts) from an object to be imaged (e.g., a human patient) that has been administered a radiopharmaceutical. The depicted imaging system 1100 includes a gantry 1110 having a bore 1112 therethrough, plural radiation detector head assemblies 1115, and a processing unit 1120.

The gantry 1110 defines the bore 1112. The bore 1112 is configured to accept an object to be imaged (e.g., a human patient or portion thereof). As seen in FIG. 16, plural radiation detector head assemblies 1115 are mounted to the gantry 1110. In the illustrated embodiment, each radiation detector head assembly 1115 includes an arm 1114 and a head 1116. The arm 1114 is configured to articulate the head 1116 radially toward and/or away from a center of the bore 1112 (and/or in other directions), and the head 1116 includes at least one detector, with the head 1116 disposed at a radially inward end of the arm 1114 and configured to pivot to provide a range of positions from which imaging information is acquired.

The detector of the head 1116, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector. The volumes of the detector under the pixelated anodes are defined as voxels. For each pixelated anode, the detector has a corresponding voxel. The absorption of photons by certain voxels corresponding to particular pixelated anodes results in charges generated that may be counted. The counts may be correlated to particular locations and used to reconstruct an image.

In various embodiments, each detector head assembly 1115 may define a corresponding view that is oriented toward the center of the bore 1112. Each detector head assembly 1115 in the illustrated embodiment is configured to acquire imaging information over a sweep range corresponding to the view of the given detector unit. Additional details regarding examples of systems with detector units disposed radially around a bore may be found in U.S. patent application Ser. No. 14/788,180, filed Jun. 30, 2015, entitled "Systems and Methods For Dynamic Scanning With Multi-Head Camera," the subject matter of which is incorporated by reference in its entirety.

The processing unit 1120 includes memory 1122. The imaging system 1100 is shown as including a single processing unit 1120; however, the block for the processing unit 1120 may be understood as representing one or more processors that may be distributed or remote from each other. The depicted processing unit 1120 includes processing circuitry configured to perform one or more tasks, functions, or steps discussed herein. It may be noted that "processing unit" as used herein is not intended to necessarily be limited to a single processor or computer. For example, the processing unit 1120 may include multiple processors and/or computers, which may be integrated in a common housing or unit, or which may distributed among various units or housings.

Generally, various aspects (e.g., programmed modules) of the processing unit 1120 act individually or cooperatively with other aspects to perform one or more aspects of the methods, steps, or processes discussed herein. In the depicted embodiment, the memory 1122 includes a tangible, non-transitory computer readable medium having stored thereon instructions for performing one or more aspects of the methods, steps, or processes discussed herein.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A radiation detector assembly comprising:
a semiconductor detector having sidewalls and a surface;
plural pixelated anodes disposed on the surface, each pixelated anode configured to generate a mixed primary signal responsive to reception of a photon by at least one surrounding anode of the pixelated anode and to generate a mixed secondary signal responsive to reception of a photon by the pixelated anode; and
at least one processor operably coupled to the pixelated anodes, the at least one processor configured to:
acquire the mixed primary signal from a first pixelated anode;
acquire the mixed secondary signal from a second pixelated anode, wherein the mixed primary signal and the mixed secondary signal are generated responsive to an event generated in the second pixelated anode and collected by the first pixelated anode; and
count an event in the second pixelated anode responsive to acquiring the mixed primary signal from the first pixelated anode and the mixed secondary signal from the second pixelated anode.

2. The radiation detector assembly of claim 1, wherein the mixed primary signal from the first pixelated anode starts as a conventional secondary signal induced by an electrical charge of an event generated in the second pixelated anode and ends as a conventional primary signal in the first pixelated anode.

3. The radiation detector assembly of claim 1, wherein the mixed secondary signal from the second pixelated anode starts as a conventional primary signal responsive to an event in the second pixelated anode and ends as a conventional secondary signal induced by an electrical charge of the event in the second pixelated anode.

4. The radiation detector assembly of claim 1, wherein the second pixelated anode is closer to a sidewall than the first pixelated anode.

5. The radiation detector assembly of claim 1, wherein the at least one processor further comprises an application specific integrated circuit (ASIC) comprising multiple electronic channels, wherein each electronic channel is coupled to a corresponding pixelated anode.

6. The radiation detector assembly of claim 5, wherein each electronic channel is set to a predetermined threshold level that is greater than 15% of the maximum of a conventional induced signal produced by a measured isotope.

7. The radiation detector assembly of claim 5, wherein each electronic channel comprises a corresponding slow shaper and a corresponding fast shaper.

8. The radiation detector assembly of claim 5, wherein at least some of the electronic channels are alternating current (AC) coupled to corresponding pixelated anodes.

9. The radiation detector assembly of claim 8, comprising at least one of first order sidewall pixelated anodes located immediately adjacent a corresponding sidewall or bad inland pixelated anodes disposed a distance from corresponding sidewalls, wherein the at least of first order sidewall pixelated anodes or bad inland pixelated anodes are AC coupled to corresponding electronic channels.

10. The radiation detector assembly of claim 9, wherein the at least one processor comprises a field programmable gate array (FPGA) configured to AC couple the corresponding electronic channels to the at least one of first order sidewall pixelated anodes or bad inland pixelated anodes.

11. The radiation detector assembly of claim 10, wherein the sidewalls are not polished.

12. The method of claim 10, wherein the sidewalls are not polished before joining the semiconductor portions.

13. A method of imaging using a semiconductor detector having sidewalls and a surface with plural pixelated anodes disposed thereon, the method comprising:
generating a mixed primary signal responsive to reception of a photon by at least one surrounding anode of a pixelated anode;
generating a mixed secondary signal responsive to reception of the photon by the pixelated anode;
acquiring the mixed primary signal from a first pixelated anode;
acquiring the mixed secondary signal from a second pixelated anode, wherein the mixed primary signal and the mixed secondary signal are generated responsive to an event generated in the second pixelated anode and collected by the first pixelated anode; and
counting an event in the second pixelated anode responsive to acquiring the mixed primary signal from the first pixelated anode and the mixed secondary signal from the second pixelated anode.

14. The method of claim 13, wherein the mixed primary signal from the first pixelated anode starts as a conventional secondary signal induced by an electrical charge of an event generated in the second pixelated anode and ends as a conventional primary signal in the first pixelated anode.

15. The method of claim 13, wherein the mixed secondary signal from the second pixelated anode starts as a conventional primary signal responsive to an event in the second pixelated anode and ends as a conventional secondary signal induced by an electrical charge of the event in the second pixelated anode.

16. The method of claim 13, wherein the second pixelated anode is closer to a sidewall than the first pixelated anode.

17. A method of providing a radiation detector assembly comprising:

forming semiconductor detector portions;

joining the semiconductor detector portions to form a semiconductor detector having sidewalls and a surface, wherein the semiconductor detector has plural pixelated anodes disposed on the surface, each pixelated anode configured to generate a mixed primary signal responsive to reception of a photon by at least one surrounding anode of the pixelated anode and to generate a mixed secondary signal responsive to reception of a photon by the pixelated anode; and coupling the semiconductor detector to at least one processor that is configured to:

acquire a mixed primary signal from a first pixelated anode;

acquire at least one mixed secondary signal from a second pixelated anode, wherein the mixed primary signal and the mixed secondary signal are generated responsive to an event generated in the second pixelated anode and collected by the first pixelated anode; and count an event in the second pixel responsive to acquiring the mixed primary signal from the first pixelated anode and the mixed secondary signal from the second pixelated anode.

18. The method of claim 17, further comprising electronic channels of an application specific integrated circuit (ASIC) to corresponding pixelated anodes.

19. The method of claim 18, wherein each electronic channel comprises a corresponding slow shaper and a corresponding fast shaper.

20. The method of claim 18, further comprising AC coupling at least some of the electronic channels to corresponding pixelated anodes.

* * * * *